United States Patent [19]
Larossa et al.

[11] Patent Number: 6,025,131
[45] Date of Patent: *Feb. 15, 2000

[54] FACILE METHOD FOR IDENTIFYING REGULATED PROMOTERS

[75] Inventors: Robert Alan Larossa, West Chester, Pa.; Tina Kangas Van Dyk, Wilmington, Del.

[73] Assignee: E. I. du Pont de Namours and Company, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 08/735,545

[22] Filed: Oct. 23, 1996

[51] Int. Cl.$^7$ .............................. C12Q 1/68; C12P 19/34; C12N 15/74; C07H 21/04

[52] U.S. Cl. .......................... 435/6; 435/91.2; 435/320.1; 435/476; 435/488; 536/23.1; 536/24.1

[58] Field of Search .......................... 435/6, 91.1, 172.3, 435/240.2, 240.4, 252.3, 320.1; 536/23.1, 24.1

[56] References Cited

U.S. PATENT DOCUMENTS 5,595,896  1/1997  Coruzzi et al. ......................... 800/298

FOREIGN PATENT DOCUMENTS

WO 90/08836  9/1990  WIPO.
WO 94/13831  6/1994  WIPO.
WO 95/15224  6/1995  WIPO.

OTHER PUBLICATIONS

McCann et al., An evaluation of Salmonella (Ames) test data in the published literature: Application of statistical procedures and analysis of mutagenic potency, Mutat. Res., 134, pp: 1–47 (1984).

Orser et al., Use of Prokaryotic Stress Promoters as Indicators of the Mechanisms of Chemical Toxicity, (In Vitro Toxicol., 8(1):71–85) Mary Ann Liebert, Inc., Publishers (1995).

Burlage et al., Monitoring of Naphthalene Catabolism by Bioluminescence with nah–lux Transcriptional Fusions, J. Bacteriology, 172(9):4749–4757 (1990).

Szittner and Meighen, Nucleotide Sequence, Expression, and Properties of Luciferase Coded by lux Genes from a Terrestrial Bacterium, J. Biol. Chem., 265:16581–16587 (1990).

Rupani et al., Characterization of the Stress Response of a Bioluminescent Biological Sensor in Batch and Continuous Cultures, Biotechnol Prog, 12:387–392 (1996).

Hill et al., Review The application of lux genes, Biotechnol. Appl. Biochem. 17:3–14 (1993).

Tatsumi et al., Molecular cloning and expression in *Escherichia coli* of a cDNA clone encoding luciferase of a firefly, *Luciola lateralis*, Biochem. Biophysica Acta. 1131:161–165 (1992).

Jacobs et al., Highly bioluminescent *Bacillus subtilis* obtained through high–level expression of a luxAB fusion gene, Mol. Gen. Genet., 230:251–256 (1991).

LaRossa et al., Physiological roles of the DnaK and GroE stress protein: catalysts of protein folding or macromolecular sponges? Mol. Microbiology, 5(3):529–534 (1991).

VanBogelen et al. Differential Induction of Heat Shock, SOS, and Oxidation Stress Regulons and Accumulation of Nucleotides in *Escherichia coli*, ( J. Bacteriology, 169(1):26–32 (1987).

Kenyon and Walker, DNA–damaging agents stimulate gene expression at specific loci in *Escherichia coli*, Proc. Natl. Acad. Sci. U.S.A., 577(5):2819–2823 (1980).

Blom et al., Unique and Overlapping Pollutant Stress Proteins of *Escherichia coli*, Appl. Environ. Microbiol., 58(1):331–334 (1992).

Simons et al., Improved single and multicopy lac–based cloning vectors for protein and operon fusions Gene, Elsevier Science Publishers B.V. GEN 01960, 53:85–96 (1987).

Engebrecht et al., Measuring Gene Expression with Light, Science, 227:1345–1347 (1985).

Carmi, O.A., et al., Use of Bacterial Luciferase to Establish a Promoter Probe Vehicle Capable of Nondestructive Real–Time Analysis of Gene Expression in Bacillus spp., J. Bacteriol., 169(5):2165–2170 (1987).

Guzzo and DuBow, Construction of stable, single–copy luciferase gene fusions in *Escherichia coli*, Arch. Microbiol., 156:444–448 (1991).

Guzzo et al., Transcription of the *Escherichia coli* fliC Gene Is Regulated by Metal Ions, Appl. Environ. Microbiol., 57(8):2255–2259 (1991).

Guzzo and DuBow, A luxAB transcriptional fusion to the cryptic celF gene of *Escherichia coli* displays increased luminescence in the presence of nickel, Mol. Gen. Genet., 242:455–460 (1994).

Kragelund et al., Isolation of lux reporter gene fusions in *Pseudomonas fluorescens* DF57 inducible by nitrogen or phosphorus starvation, FEMS Microbiol. Ecology, 17:95–106 (1995).

(List continued on next page.)

Primary Examiner—John S. Brusca
Assistant Examiner—William Sandals

[57] ABSTRACT

A new method for the identification of useful promoters is disclosed. The method is capable of identifying bacterial promoters sensitive to a particular cellular insult and may be modified to identify promoters sensitive to herbicides and crop protection chemicals. Constructs comprising promoters upstream of a luminescent reporter genes are placed in transformed hosts. Transformants grown in liquid media to a predetermined growth stage and contacted with a cellular insult are assessed for regulatory region activity by measurement of the resulting change in bioluminesence. The method is able to identify promoters undetectable by standard methods.

11 Claims, 6 Drawing Sheets

(1 of 6 Drawing Sheet(s) Filed in Color)

OTHER PUBLICATIONS

Waterfield et al. The isolation of lactococcal promoters and their use in investigating bacterial luciferase synthesis in *Lactococcus lactis,* Gene, 165:9–15 (1995).

Shen and Keen. Characterization of the promoter of avirulence gene D form Pseudomonas Syringae pv. tomato. J. Bact. vol. 175(18):5916–5924, Sep. 1993.

Barnes. Variable patterns of expression if luciferase in transgenic tobacco leaves. PNAS (USA). vol. 87:9183–9197, Dec. 1990.

Cebolla et. al.. Expression vectors for the use of eukaryotic luciferases as bacterial markers with different colores of luminescence. Appl. and Environ. Microbiol. vol. 61(2):660–668, Feb. 1995.

Weltring. A method for easy isolation of promoter fragments from promoter–probe libraries of filamentous fungi. Curr. Genet. 28:190–196, Aug. 17, 1995.

FACILE METHOD FOR IDENTIFYING REGULATED PROMOTERS

FIELD OF INVENTION

The invention relates to the discovery and characterization of regulated promoters aided by use of reporter gene fusions. More specifically the invention creates gene fusions comprising bioluminescent reporter genes in transformed hosts grown in liquid media to identify regulated promoters.

BACKGROUND OF THE INVENTION

Technological advances within the chemical arts supporting the agrochemical, pharmaceutical and environmental industries have made possible the synthesis of vast arrays of chemical compounds. The utility of these compounds is modeled on various structure-function relationships. Compound utility is often confirmed through screening methods designed to associate these compounds with desired known activities. Currently, methods of synthesis are capable of producing far more compounds than can be reasonably screened. A need exists for the development of rapid high-throughput screens that are able to analyze vast numbers of compounds for putative agrochemical, environmental, or pharmaceutical activities.

Current screening methods are often costly, time intensive, and lacking in specificity where the screens must rely on studies in whole plants and animals. A variety of methods have been developed using engineered microorganisms to detect and characterize compound activity. One such test is the Ames test (McCann et al. *Mutat. Res.* (1984), 134(1), 1–47) where Salmonella sp. are used to characterize compounds as mutagenic or pro-mutagenic. The Ames test relies on the unique enzymatic properties of *S. typhimurium* to characterize xenobiotics as mutagens or pro-mutagens. Other micrqorganism-based systems for the characterization of compounds have relied on the specificity of gene promoters or regulatory regions to identify potential compound activity. For example, Orser et al. (*In Vitro Toxicol.* (1995), 8(1):71–85) utilizes a stress promoter fused to a promoter-less lacZ structural gene to screen compounds for environmental toxicity, Molders et al. (WO 9008836) teaches the use of recombinant bacteria to detect the presence of mercury using a gene complex consisting of a mer regulatory region that is hypersensitive to induction by mercury and Burlage et al. (*J. Bacteriol*, 172 (9):4749–4757 (1990)) recites a method using a naphthalene sensitive regulatory region from plasmid NAH7 to detect naphthalene-like compounds.

Microbiological methods such as these hold great promise for the screening of compounds for specific activities; however they are impeded by the lack of a facile reporting system and by the difficulty in identifying regulatory regions specific for the activities to be screened for. A rapid method for the identification of new, compound sensitive regulatory regions combined with a facile reporting gene would represent a significance advance in the art of compound screens. Genes responsible for bacterial bioluminescence are gaining increasing interest as facile reporters and offer a partial solution to the development of rapid high-throughput screens for new compound activities.

Bioluminescent bacteria are found in marine and terrestrial environments. The lux gene products from marine organisms often exhibit thermolability such that they do not function well at typical growth temperatures for other bacteria (Szittner and Meighen, *J. Biol. Chem.*, 265:16581–16587 (1990); Rupani et al., *Biotechnol Prog*, 12:387–392 (1996); Hill et al., *Biotechnol Appl Biochem*, 17:3–14 (1993)). In contrast, the lux gene products from the terrestrial microorganism *Photorhabdus luminescens* (formerly called *Xenorhabdus luminescens*) are stable at temperatures up to 45° C. (Szittner and Meighen, *J. Biol. Chem.*, 265:16581–16587 (1990)). Therefore, the advantage of the thermostable lux genes is that a larger range of assay temperatures are available for use.

Recent advances in recombinant DNA technology have made it possible to express the luciferase (lux) gene complex as heterologous gene products. This is generally accomplished by placing the lux structural gene complex under the control of a host promoter. So, for example, cDNA encoding firefly luciferase has been expressed in *E. coli* under the control of the lacZ promoter. (Tatsumi et al., *Biochem. Biophys Acta.*, 1131, 2:161–165, (1992)), and the luxAB fusion gene has been expressed in Bacillus at levels comparable to those achievable in *E. coli* by placing it under the control of the powerful Pxyn promoter (Jacobs et al., *Mol. Gen. Genet.*, 230(1–2):251–256, (1991)).

Stress genes are found in all cells and are defined as those genes activated as a result of any type of insults that might alter the normal cellular metabolism. Environmental insults often induce synthesis of an overlapping set of proteins. The most well recognized class of stress genes are the heat shock genes encoding a set of cellular proteins thought to have roles in refolding, recycling and resynthesis of proteins. The heat shock phenomenon was first described as a response to an increased temperature. Subsequent work has shown that exposure to a variety of insults including phage infection, macrophage envelopment, as well as the presence of organic molecules and heavy metals can also trigger the heat shock response. The common theme of the inducing agents may be unfolding of some proteins within the cell. (LaRossa et al., *Mol. Micriobiol.*, 5(3):529–534, (1991)). Thus the response may integrate and report a wide range of environmental insults. VanBogelen et al. (*J. Bacteriol.*, 169(1):26–32, (1987)) have demonstrated that a variety of chemicals are able to induce the heat shock genes in *E. coli*, including $CdCl_2$, $H_2O_2$, ethanol, puromycin and nalidixic acid. Blom et al., (*Appl. Environ. Microbiol.*, 58(1):331–334, (1992)) teach that the exposure of *E. coli* cultures to benzene, $CdCl_2$, chlorpyrivos, 2,4-dichloraniline, dioctylphtalate, hexachlorobenzene, pentachlorophenol, trichloroethylene, and tetrapropylbenzosulfonate leads to the induction of up to 39 different stress proteins, as analyzed by two dimensional gel electrophoresis. LaRossa et al. (PCT International Application WO 94/13831) have transformed *E. coli* with a construct comprised of luxCDABE operably linked to a variety of stress promoters. They have used the microorganisms to detect a variety of environmental insults such as ethanol, $CdCl_2$, and toluene. The presence of a sublethal concentration of the insult is indicated by an increase in bioluminescence. The detector organism described in WO 94/13831 was also used in a lyophilized form to detect similar environmental stresses by an increase in bioluminescence (Van Dyk, T. and Wagner, W., International Application No. PCT/US 95/15224.

Since the cell attempts to maintain a steady state, stress responses are activated well below the minimal inhibitory concentration for any condition that serves as a triggering factor. It would be useful to identify complete sets of promoters induced by any particular stress.

Thus, genes responsible for bacterial bioluminescence offer a partial solution to the need for a microorganism-based screening method for compound activity. Still needed, however, is a rapid method for the identification of useful regulatory regions.

Various methods of screening for bacterial promoter activity and for regulatory regions affected by various conditions are known. It is very common to use reporter genes for such a task. For example, transposons which can be inserted throughout the genome can be engineered to have reporter genes that require an external promoter sequence to be expressed and hence activity of the reporter gene is indicative of transcription initiated at the upstream chromosomal promoter sequences. A classic example of this approach is the work of Kenyon and Walker in discovering genes induced by DNA damage (Kenyon and Walker, *Proc. Natl. Acad. Sci. U.S.A.*, 77:2819–2823 (1980)). Many such transposons are available and have been recently reviewed (Berg and Berg, *Transposable element tools for microbial genetics, in Escherichia coli and Salmonella Cellular and Molecular Biology*, p. 2588–2612, F. C. Neidhardt, Editor. 1996, ASM Press:Washington, DC). Alternatively, plasmids with reporter genes lacking promoter activity have also been used to discover promoters, such as the vectors described by Simons et al., *Gene*, 53:85–96 (1987)). These plasmids have a multiple cloning site (MCS) upstream of the lacZYA operon that lacks its normal promoter. Just upstream of the MCS were placed multiple transcription terminators so that transcription initiated at other places on the plasmid would terminate prior to the lacZ reporter gene.

One of the reporters of transcriptional activity frequently used in transposons and plasmids are the bacterial lux genes (Engebrecht et al., *Science*, 227:1345–1347 (1985)). The lux reporter is distinct because the reporter gene products' activity, light production, can be measured without disrupting the cell. Furthermore, if the five gene luxCDABE reporter system is used, continuous monitoring of light production is possible without adding substrate exogenously. However, previous use of lux reporters for discovery of promoters have not taken advantage of such continuous monitoring and have, in general, qualitatively estimated promoter activity by the light production on petri plates (Carmi, O.A., et al., *J. Bacteriol.*, 169:2165–2170 (1987); Guzzo and DuBow, *Arch. Microbiol.*, 156:444–448 (1991); Guzzo et al., *Appl. Environ. Microbiol.*, 57:2255–2259 (1991); Guzzo and DuBow, *Mol. Gen. Genet.*, 242:455–460 (1994); Kragelund et al., *FEMS Microbiol. Ecol.*, 17:95–106 (1995); Waterfield et al., *Gene*, 165:9–15 (1995)).

These previously used methods of screening for lux reporter activity on petri plates have been limited by being restricted to growth conditions and averaged stages of growth of bacterial cells within colonies on solidified medium. It was also not possible to apply a stress condition and quickly visualize changes in gene expression.

The problem to be overcome, therefore is a method for the identification of gene regulatory regions, responsive to a particular cellular stress, such as that produced by herbicides or crop protection chemicals. Applicants have solved the stated problem by randomly fusing regulatory regions to a bacterial luminescent gene complex where contacting the fusion in a suitable host with a cellular insult producing a cellular stress results in detection of that cellular stress by an increase in cellular luminescence. Applicants method of screening in liquid medium has the additional advantage of being able to detect regulatory regions that cannot be discovered by current methods, which are restricted to screening on the basis of colony formation on solid medium. The versatility of being able to screen for stress or chemical responsive regulatory regions rapidly and in a growth phase of the investigators choice represents a clear advance in the art.

SUMMARY OF THE INVENTION

Applicants have provided a method for identifying regulatory regions modulated by a cellular insult in a specific gene pool having the steps:

(i) creating a library of gene fusions to a luminescent reporter gene complex in suitable bacteria to create fusion-containing strains;

(ii) culturing individual gene fusion-containing strains in liquid media;

(iii) contacting the fusion-containing strains at a particular growth phase with a cellular insult for which the fusion-containing strain is known to be sensitive; and (iv) analyzing the fusion-containing strain for a change in luminescence relative to a baseline luminescence, said change in luminescence indicating that the regulatory region is modulated by the cellular insult.

In particular, the method permits recovering the fusion-containing strains containing a regulatory region modulated by the cellular insult.

The method uses a luminescent reporter gene complex selected from the group consisting of a bacterial lux gene complex, a gene complex encoding luciferase from Renella species, and a luc gene complex, and more particularly, a thermostable lux gene complex or a luxCDABE gene complex.

The method can be used with any cellular insult, more particularly, with a crop protection chemical such as sulfometuron methyl (SM), one member of the class of N-(heterocyclicaminocarbonyl)sulfonamide-containing herbicidal chemical compounds.

Particular embodiments of the invention include 1) an *E. coli* 1.9 kb genomic segment containing an SM-responsive regulatory region, said genomic segment bounded by SEQ ID NO:1 and SEQ ID NO:2; 2) an *E. coli* 1.4 kb genomic segment containing an SM-responsive regulatory region, said genomic segment bounded by SEQ ID NO:15 and SEQ ID NO:16; 3) an *E. coli* 1.8 kb genomic segment containing an SM-responsive regulatory region, said genomic segment bounded by SEQ ID NO:1 1 and SEQ ID NO:12; and 4) an *E. coli* 1.6 kb genomic segment containing an SM-responsive regulatory region, said genomic segment bounded by SEQ ID NO:19 and SEQ ID NO:20.

The invention also encompasses plasmids comprising:

(i) an *E. coli* genomic segment containing an SM-responsive regulatory region operably linked to a thermostable luxCDABE gene complex; and (ii) a transcription terminator region upstream of said promoter.

The particular plasmids have an *E. coli* genomic segment bounded by unique pairs of DNA fragments selected from the group consisting of SEQ ID NOS:1 and 2, SEQ ID NOS:3 and 4, SEQ ID NOS:5 and 6, SEQ ID NOS:7 and 8, SEQ ID NOS:9 and 10, SEQ ID NOS: 11 and 12, SEQ ID NOS:13 and 14, SEQ ID NOS:15 and 16, SEQ ID NOS:17 and 18, SEQ ID NOS:19 and 20, SEQ ID NOS:21 and 22, SEQ ID NOS:23 and 24, and SEQ ID NOS:25 and 26.

The invention also encompasses transformants comprising a suitable host cell and the disclosed plasmid wherein the transformant is sensitive to SM.

The suitable host cell used in the transformant is a bacteria classified in the Family *Enterobacteriaceae*, and particularly preferred is *Escherichia coli.*

A further embodiment of the invention is a method to detect chemical compounds potentially useful as a crop protection chemical having the steps:

(i) contacting the chemical compound with a detector organism containing a genomic segment comprising a responsive regulatory region operably linked to a luminescent reporter gene complex;

(ii) measuring an increase in bioluminescence in the detector organism, the increase in bioluminescence indicating that the chemical compound is potentially useful as a crop protection chemical.

The genomic segments useful in the invention are selected from the group consisting of a) an *E. coli* 1.9 kb genomic segment containing an SM-responsive regulatory region, said segment bounded by SEQ ID NO:1 and SEQ ID NO:2; b) an *E. coli* 1.4 kb genomic segment containing an SM-responsive regulatory region, said segment bounded by SEQ ID NO:3 and SEQ ID NO:4; c) an *E. coli* 1.9 kb genomic segment containing an SM-responsive regulatory region, said segment bounded by SEQ ID NO:5 and SEQ ID NO:6; d) an *E. coli* 1.3 kb genomic segment containing an SM-responsive regulatory region, said segment bounded by SEQ ID NO:7 and SEQ ID NO:8; e) an *E. coli* 2.5 kb genomic segment containing an SM-responsive regulatory region, said segment bounded by SEQ ID NO:9 and SEQ ID NO:10; f) an *E. coli* 1.8 kb genomic segment containing an SM-responsive regulatory region, said segment bounded by SEQ ID NO:11 and SEQ ID NO:12; g) an *E. coli* 1.2 kb genomic segment containing an SM-responsive regulatory region, said segment bounded by SEQ ID NO:13 and SEQ ID NO:14; h) an *E. coli* 1.4 kb genomic segment containing an SM-responsive regulatory region, said segment bounded by SEQ ID NO:15 and SEQ ID NO:16; i) an *E. coli* 1.3 kb genomic segment containing an SM-responsive regulatory region, said segment bounded by SEQ ID NO:17 and SEQ ID NO:18; j) an *E. coli* 1.6 kb genomic segment containing an SM-responsive regulatory region, said segment bounded by SEQ ID NO:19 and SEQ ID NO:20; k) an *E. coli* 1.9 kb genomic segment containing an SM-responsive regulatory region, said segment bounded by SEQ ID NO:21 and SEQ ID NO:22; l) an *E. coli* 1.0 kb genomic segment containing an SM-responsive regulatory region, said segment bounded by SEQ ID NO:23 and SEQ ID NO:24; and m) an *E. coli* 2.0 kb genomic segment containing an SM-responsive regulatory region, said segment bounded by SEQ ID NO:25 and SEQ ID NO:26.

Gene fusions useful in the invention include those a) comprising the SM-responsive regulatory region contained within the *E. coli* 1.9 kb genomic segment, the SM-responsive regulatory region operably linked to a luminescent reporter gene complex; b) comprising the SM responsive regulatory region contained within the genomic segment bounded by SEQ ID NO:3 and SEQ ID NO:4, the regulatory region operably linked to a luminescent reporter gene complex; c) comprising the SM-responsive regulatory region contained within the genomic segment bounded by SEQ ID NO:5 and SEQ ID NO: 6, the regulatory region operably linked to a luminescent reporter gene complex; d) comprising the SM-responsive regulatory region contained within the genomic segment bounded by SEQ ID NO:7 and SEQ ID NO:8, said regulatory region operably linked to a luminescent reporter gene complex; e) comprising the SM responsive regulatory region contained within the genomic segment bounded by SEQ ID NO:9 and SEQ ID NO: 10, the regulatory region operably linked to a luminescent reporter gene complex; f) comprising the SM-responsive regulatory region contained within the *E. coli* 1.8 kb genomic segment, the regulatory region operably linked to a luminescent reporter gene complex; g) comprising the SM-responsive regulatory region contained within the genomic segment bounded by SEQ ID NO:13 and SEQ ID NO:14, said regulatory region operably linked to a luminescent reporter gene complex; h) comprising the SM-responsive regulatory region contained within the *E. coli* 1.4 kb genomic segment the regulatory region operably linked to a luminescent reporter gene complex; i) comprising the SM-responsive regulatory region contained within the genomic segment bounded by SEQ ID NO:17 and SEQ ID NO:18, the regulatory region operably linked to a luminescent reporter gene complex; j) comprising the SM-responsive regulatory region contained within the *E. coli* 1.7 kb genomic segment, the regulatory region operably linked to a luminescent reporter gene complex; k) comprising the SM-responsive regulatory region contained within the genomic segment bounded by SEQ ID NO:21 and SEQ ID NO:22, the regulatory region operably linked to a luminescent reporter gene complex; l) comprising the SM-responsive regulatory region contained within the genomic segment bounded by SEQ ID NO:23 and SEQ ID NO:24, the regulatory region operably linked to a luminescent reporter gene complex; and m) comprising the SM-responsive regulatory region contained within the genomic segment bounded by SEQ ID NO:25 and SEQ ID NO:26, the regulatory region operably linked to a luminescent reporter gene complex.

BRIEF DESCRIPTION OF DRAWINGS, BIOLOGICAL DEPOSITS, AND SEQUENCE LISTING

The file of this patent contains at least one drawing executed in color. Copies of this patent with color drawing will be provided by the Patent and Trademark Office upon request and payment of the necessary fee.

Figure 1:
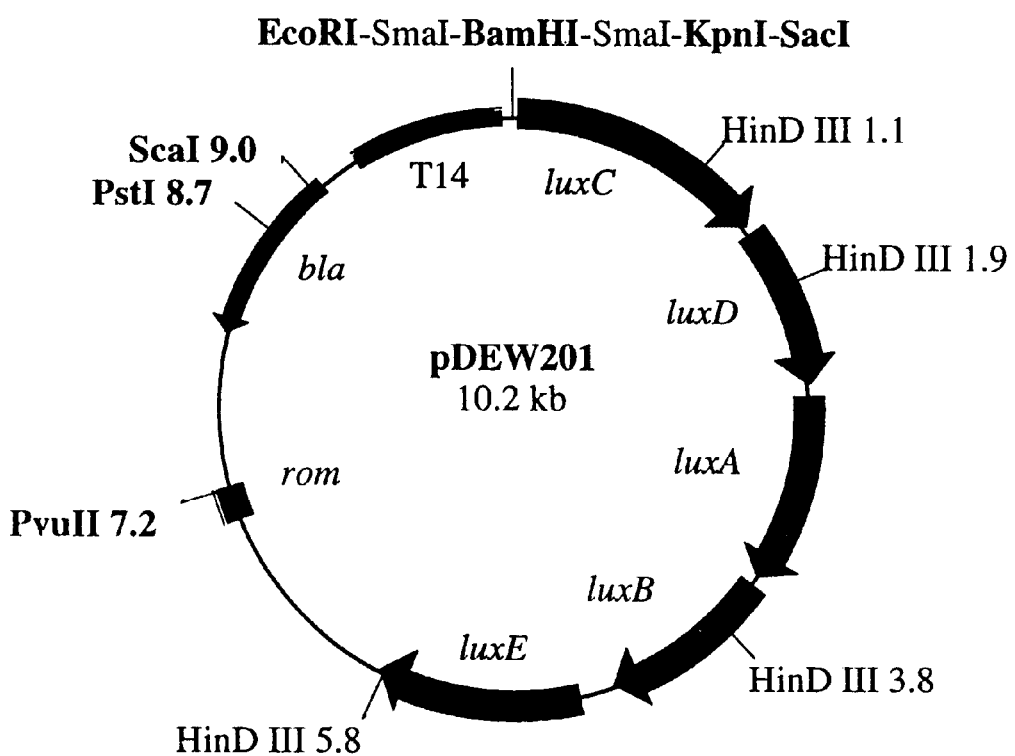
FIG. 1 shows the restriction sites and genes of plasmid pDEW201, a promoter probe vector.

Applicants have made the following biological deposits under the terms of the Budapest Treaty on the International Recognition of the Deposit of Micro-organisms for the Purposes of Patent Procedure:

| Depositor Identification Reference | Int'l. Depository Designation | Date of Deposit |
|---|---|---|
| *Escherichia coli* DPD2083 (host strain DPD1675 containing plasmid PDEW201) | ATCC 98227 | 16 October 1996 |

"ATCC" refers to the American Type Culture Collection international depository located at 10801 University Blvd., Manassas, Va. 20110-2209, U.S.A. The designations refer to the accession number of the deposited material.

Applicants have provided 28 sequences in conformity with Rules for the Standard Representation of Nucleotide and Amino Acid Sequences in Patent Applications (Annexes I and II to the Decision of the President of the EPO, published in Supplement No. 2 to OJ EPO, 12/1992) and with 37 C.F.R. 1.821–1.825 and Appendices A and B (Requirements for Application Disclosures Containing Nucleotides and/or Amino Acid Sequences).

DETAILED DESCRIPTION OF THE INVENTION

Applicants have solved the significant problem of how to identify regulatory regions affected by cellular stress such as that created to crop protection chemicals in cells growing in a specified growth phase in a liquid medium. The solution involves analyzing luminescence and changes in luminescence following stress of cells grown to a specified growth phase in liquid medium. Using this method, promoters encompassing >1000-fold range of activity were readily found, which is far greater than the range of promoter activities found by previously used methods. For example, Waterfield et al (Waterfield, et al., Gene, 165:9–15 (1995)) using standard colony formation methods found promoters in *Lactococcus lactis* encompassing only a 71-fold range of activity. Furthermore, several genetic fusions to previously uncharacterized or unknown genes of *E. coli* were found by this method. Thus the instant method is able to detect promoters or stress responsive regulatory regions undetectable by current methods.

Utility Statement

The present invention provides a method of discovery and characterization of promoter regions using probe vectors that use a bioluminescent reporter gene complex. Isolated chromosomal DNA is digested with a restriction enzyme to give overlapping fragments, which are subsequently ligated upstream of the reporter genes. Those DNA sequences containing promoters will result in transcription and subsequent translation of the reporter gene products and hence light production from cells containing the fusion plasmid. Quantitation of this bioluminescence results in identification of sequences with promoter activity.

The following definitions are used herein and should be referred to for claim interpretation.

The term "bioluminescence" refers to the phenomenon of light emission from any living organism.

The term "baseline bioluminescence" refers to light emission of a microorganism in the absence of stress.

The term "lux" refers to the lux structural genes which include luxA, luxB, luxC, luxD and luxE and which are responsible for the phenomenon of bacterial bioluminescence. A lux gene complex might include all of the independent lux genes, acting in concert, or any subset of the lux structural genes so long as luxA and luxB are part of the complex.

The term "stress" or "cellular stress" refers to the condition produced in a cell as the result of exposure to a cellular insult. A "cellular insult" may be any substance or change in the cellular environment that results in an alteration of normal cellular metabolism in a bacterial cell or population of cells. Such cellular insults may include, but are not limited to, chemicals (such as herbicides, crop protection chemicals, environmental pollutants, heavy metals), physical treatments such as changes in temperature, changes in pH, agents producing oxidative damage or DNA damage (such as from UV exposure), anaerobiosis, biological insults such as the introduction of other life forms (viruses, bacteria, etc.) into the bacterial culture, or changes in nutrient availability.

A "luminescent reporter gene complex" means any reporter gene or genes the products of which result in light production, such as the bacterial lux genes, the firefly (for example, *Photinus pyralis*), or click beetle (for example, *Pyrophorus plagiophthalamus*) luciferase genes (luc), or the gene encoding the luciferase from the sea pansy, *Renilla reniformis*.

"Host cell sensitivity" is a characteristic of a bacterial strain such that its metabolic activity is inhibited by addition of a chemical compound, biological entity, or physical treatment.

The term "multiple cloning site" (MCS) refers to a genetic element in which multiple sites of restriction endonuclease cleavage are embedded.

The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene. In this method, promoters are defined by their ability to result in expression of the reporter gene complex when cloned upstream of the reporter genes. Furthermore, activation of the promoter by a stress is defined as an increase of activity of the reporter gene complex following application of the stress.

A "fragment" constitutes a fraction of the DNA sequence of the particular region.

"Gene fusion" is a hybrid DNA fragment comprising a regulatory signal essential for transcription (referred to as a promoter) fused to at least one structural gene sequence coding for a specific polypeptide.

The term "genomic segment" refers to a DNA fragment containing a gene regulatory region. Genomic segments of the present invention are typically derived from the *E. coli* genome and contain regulatory regions responsive to a variety of cellular insults including those produced by contact with crop protection chemicals and herbicides.

The term "regulatory region" refers to a DNA fragment containing any of the genetic elements responsible for directing gene transcription and translation, including promoter or initiation control regions, coding regions, open reading frames (ORF) and transcriptional termination regions. Regulatory regions may be positively activated by a variety of stimuli resulting in up-regulation of genes and an increase in transcription. "Regulation" and "regulate" refer to the modulation of gene expression controlled by DNA sequence elements located primarily, but not exclusively upstream of (5' to) the transcription start of a gene. Regulation may result in an all-or-none response to a stimulation, or it may result in variations in the level of gene expression. In the context of the present invention, regulatory regions activated by or responsive to sulfometuron methyl ("SM-responsive") were identified. For a review of regulation of bacterial genes see *Escherichia coli and Salmonella Cellular and Molecular Biology*, (1225–1309), F. C. Neidhardt, Editor. 1996, ASM Press:Washington, D.C.).

The term "coding sequence" refers to that portion of a gene encoding a protein, polypeptide, or a portion thereof, and usually excluding the regulatory sequences which drive the initiation of transcription. A coding sequence may be one normally found in the cell or it may be one not normally found in a cellular location, but one that is instead introduced, in which case it is termed a heterologous gene. The coding sequence may be a composite of fragments derived from different sources, naturally occurring or synthetic.

The term "operably linked" refers to the fusion of two fragments of DNA in a proper orientation to be transcribed into functional RNA.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the thus transcribed messenger RNA is translated into the above-mentioned gene product if the gene product is a protein.

The term "plasmid" or "vector" as used herein refers to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Plasmid pDEW201 has the unique features of carrying the *Photorhabdus luminescens* luxCDABE genes without a promoter, upstream of which are transcription terminator sequences and a MCS. The derivatives of pDEW201 described herein contain *E. coli* chromosomal DNA cloned into the MCS.

The term "restriction endonuclease" or "restriction enzyme" refers to an enzyme which binds and cuts within a specific nucleotide sequence within double-stranded DNA.

"Liquid media" refers to microbial growth medium that is not solidified, such as by addition of agar.

"Growth phase" refers to stages of bacterial cell growth of the cells in liquid medium which allows for a uniform population of cells to be produced. Examples of growth phases include such as early log phase, mid log phase, late log phase or stationary phase.

The term "log phase" or "log phase growth" refers to cell cultures of detector organisms growing under conditions permitting the exponential multiplication of the detector cell number.

The term "Relative Light Unit" is abbreviated "RLU" and refers to a measure of light emission as measured by a luminometer, calibrated against an internal standard unique to the luminometer being used.

The term "crop protection chemical" or "CPC" refers to compounds having toxic or repellent effect on insects, plant pathogens, or crop-competing plant species known to damage crop plants. CPC includes pesticides (paraquat, copper sulfate, metidathion), anti-pathogenic compounds such as fungicides (chlorothalonil) or responsible for insect behavior modulation (pheromones, allomones and kairomones), and herbicides referring to compounds having specific or general toxicity to plant species. Typical herbicides include but are not limited to the class of sulfonylurea herbicides and sulfonanilide herbicides (chlorsulfuron, triasulfuron, metsulfuron-methyl), auxin herbicides (e.g. dicamba, 2-methyl-4-chlorophenoxyacetic acid, picloram, quinclorac, quinmerac), pre-emergence herbicides (metribuzin), and post-emergence herbicides (Clethodim Pendimethalin, oryzalin, dithiopyr, oxadiazon, prodiamine, 2-4-D).

"Sulfonylurea herbicides" are defined as N-(heterocyclicaminocarbonyl)-arylsulfonamide-containing herbicidal compounds that inhibit the enzyme acetolactate synthase, such as sulfometuron methyl.

The term "sulfometuron methyl" refers to 2-[[[[(4,6-dimethyl-2-pyrimidinyl)amino]carbonyl]amino]sulfonyl]benzoic acid, methyl ester (CAS registry number 74222-97-2), and is abbreviated as "SM".

The term "sulfometuron methyl inducible promoter" is a promoter that is activated by the presence of sulfometuron methyl.

The term "detector organism" refers to an organism which contains a gene fusion consisting of a promoter fused to a structural gene and which is capable of expressing the lux gene products in response to cellular stress. Typical detector organisms include but are not limited to bacteria.

"Enteric bacteria" are members of the family *Enterobacteriaceae*, and include such members as Escherichia, Salmonella, and Shigella. They are gram-negative straight rods, 0.3–1.0×1.0–6.0 µm, motile by peritrichous flagella, except for Tatumella, or nonmotile. They grow in the presence and absence of oxygen and grow well on peptone, meat extract, and (usually) MacConkey's media. Some grow on D-glucose as the sole source of carbon, whereas others require vitamins and/or mineral(s). They are chemoorganotrophic with respiratory and fermentative metabolism but are not halophilic. Acid and often visible gas is produced during fermentation of D-glucose, other carbohydrates, and polyhydroxyl alcohols. They are oxidase negative and, with the exception of *Shigella dysenteriae* 0 group 1 and *Xenorhabdus nematophilus*, catalase positive. Nitrate is reduced to nitrite except by some strains of Erwinia and Yersina. The G +C content of DNA is 38–60 mol % ($T_m$, Bd). DNAs from species from species within most genera are at least 20% related to one another and to *Escherichia coli*, the type species of the family. Notable exceptions are species of Yersina, Proteus, Providenica, Hafnia and Edwardsiella, whose DNAs are 10–20% related to those of species from other genera. Except for *Erwinia chrysanthemi* all species tested contain the enterobacterial common antigen (Bergy's Manual of Systematic Bacteriology, D. H. Bergy, et al., Baltimore: Williams and Wilkins, 1984).

The term "transformation" refers to the stable acquisition of new genes in a cell following incorporation of nucleic acid.

"Transformant" refers to the strain that results from transformation.

Reporter Genes

The preferred reporter gene for the present invention is the lux gene complex, responsible for bacterial bioluminescence and isolated from the bacteria Photorhabdus luminescens. Bacterial bioluminescence is the phenomenon in which the products of 5 structural genes (luxA, luxB, luxC, luxD and luxE) work in concert to produce light. The luxD product generates a $C_{14}$ fatty acid from a precursor. The $C_{14}$ fatty acid is activated in an ATP dependent reaction to an acyl-enzyme conjugate through the action of the luxE product which couples bacterial bioluminescence to the cellular energetic state. The acyl-enzyme (luxE product) serves as a transfer agent, donating the acyl group to the luxC product. The acyl-LuxC binary complex is then reduced in a reaction in which NADPH serves as an electron pair and proton donor reducing the acyl conjugate to the $C_{14}$ aldehyde. This reaction couples the reducing power of the cell to bacterial light emission. The light production reaction, catalyzed by luciferase (the product of luxA and luxB), generates light. The energy for light emission is provided by the aldehyde to fatty acid conversion and $FMNH_2$ oxidation, providing another couple between light production and the cellular energy state.

The source of the bacterial lux complex was the pJT205 plasmid (formerly called pCGLS205) containing the *Photorhabdus luminescens* luxCDABE gene complex, fully described by (Rosson, R. A., PCT *International Application* WO 93/03179 (1993)).

Other reporter genes or gene complexes could also be used. Examples include but are not limited to the lux genes from marine microorganisms such as *Vibrio fischeri*, *Vibrio harveyi*, or *Photobacterium phosphoreurm*, or the genes encoding luciferases from insects such as *Photinus pyralis* or *Pyrophorus plagiophthalamus* or the sea pansy, *Renilla reniformis*.

Vectors

The invention provides a transformation vector containing a lux gene fusion, capable of transforming a bacterial host cell for the expression of the Lux proteins. A variety of transformation vectors may be used, however, those capable of transforming E. coli are preferred. pDEW201 is a specific example of a suitable transformation vector whose construction is given in detail in the following text. This vector represents only a sample of the total number of vectors created for the purpose of introducing promoter-lux reporter fusions into host cells. However, it will be readily apparent to one of skill in the art of molecular biology that the methods and materials used in their construction are representative of all other vectors described.

Transformation vectors such as these are common and construction of a suitable vector may be accomplished by means well known in the art. The preferred source of the lux genes is a pre-existing plasmid containing a promoterless lux gene complex.

Methods of creating gene fusions

The present invention provides a method for creating gene fusions where a gene regulatory region (typically comprising a promoter) is responsive to some cellular stress, is fused to a luminescent reporter gene complex. Fusions of the present invention may be created by a variety of methods including partial restriction digests of genomic DNA, PCR, LCR or strand displacement amplification of known regions of the genome or by in vitro transposition.

Restriction Digests

The preferred method of generating gene fusions is isolation of chromosomal DNA from a bacterial species, partial digestion of that chromosomal DNA yielding overlapping fragments with a restriction enzyme such that compatible sticky ends to a site in the MCS of the plasmid vector are generated, size separation by agarose gel electrophoresis, isolation of the digested chromosomal DNA in particular size ranges, and ligation into the plasmid vector which had been digested with a restriction enzyme that cuts uniquely in the MCS. Any restriction enzyme or enzymes may be used that are specific to the genomic DNA employed and will give fragments of suitable size and having compatible ends for cloning into the appropriate vector. Restriction enzymes suitable for restriction of enteric bacterial are well known in the art (Sambrook, supra) and include AluI, AvrI, BalI, BamHI, AcII, BglI, ClaI, EcoRI, EcoRV, FokI, HaeII, HaeIII, HincII, HindIII, KpnI, MboI, MboII, NciI, NcoI, NdeI, NheI, NotI, PstI, PvuI, SacI, SacII, Sau3AI, Sau96I, SfiI, SmaI, XbaI, and XhoI.

PCR—primer directed methods

Gene fusions may alternatively be generated by methods of primer directed amplification if some or all of the sequence of the desired promoter or gene is known. Methods of primer directed amplification are well known in the art and include polymerase chain reaction (PCR), ligase chain reaction (LCR) or Strand Displacement Amplification (SDA). If PCR methodology is selected, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis et al.) and U.S. Pat. No. 4,683,195 (1986, Mullis et al.). If LCR methodology is selected, then the nucleic acid replication compositions would comprise, for example, a thermostable ligase, e.g., T. aquaticus ligase, two sets of adjacent oligonucleotides wherein one member of each set is complementary to each of the target strands, Tris HCl buffer, KCl, EDTA, NAD, dithiothreitol and salmon sperm DNA. (See, for example, Tabor, S. and Richardson, C. C. (1985) Proc. Acad. Sci. USA 82, 1074–1078.) If the SDA methodology is used, amplification may be accomplished using either one or two short primers containing a site for HincII digestion, an exonuclease deficient DNA polymerase, HincII restriction enzyme and the bases dGTP, dCTP, dTTP and deoxyadenosine 5'[α-thio]triphosphate (dATP[αS]). The SDA protocol including the necessary materials is outlined in Walker et al. (Proc. Natl. Acad. Sci. USA., 89:392 (1992)).

PCR methods could also be used to generate random segments of DNA if random primers are used with bacterial chromosomal DNA as the template. Such randomly amplified DNA segments (RAPD) would then be ligated into the MCS of the desired plasmid vector.

Transposons

Transposons may also be used to generate collections of gene fusions, using a process of in vivo transposition. Many transposable elements are available that have reporter genes lacking promoter sequences (Berg and Berg, *Transposable element tools for microbial genetics*, in *Escherichia coli and Salmonella Cellular and Molecular Biology*, (2588–2612), F. C. Neidhardt, Editor. 1996, ASM Press: Washington, D.C.). Insertion of such transposons randomly throughout a bacterial chromosome will result in chromosomal promoters driving the expression of the reporter gene of the transposon.

Transformation of Suitable Hosts

Once suitable plasmids are constructed they are used to transform appropriate host cells. Introduction of the plasmid into the host cell may be accomplished by known procedures such as by transformation, e.g., using calcium-permeabilized cells, electroporation, transduction, or by transfection using a recombinant phage virus. (Sambrook et al., supra)

In the present invention, plasmid pDEW201 containing random chromosomal DNA was used to transform the E. coli DPD1675 as fully described in the GENERAL METHODS and EXAMPLES.

Transformed hosts—Detector organisms

Detector organisms may include a variety of both prokaryotic and eukaryotic organisms. Prefered are enteric bacteria; most preferred is E. coli.

A suitable bacterial strain with which to test the effects of a chemical is one whose growth is affected by that chemical. Hence, the chemical of interest must be able to enter the cell, be retained in the cell, and interact with target molecules of the cellular machinery. Various mutations of E. coli are known to affect permeation into and accumulation within the cell. Strains carrying mutant alleles of rfa (Ames et al., Proc. Nat. Acad. Sci. USA, 70(3):782–786 (1973)), envA (Young and Silver, J. Bacteriol., 173:3609–3614 (1991)), imp (Sampson et al., Genetics, 122:491–501 (1989)), lpp (Giam et al. J. Biol. Chem., (259):5601–5605 (1984)) or surA (Tormo et al., J. Bacteriol., (172):4339–4347 (1990)) have increased sensitivity to a variety of chemicals. Destruction of efflux pumps, with mutations such as emr (Ma et al., Mol. Microbiol., 16:45–55 (1995)), or acrAB (Paulsen et al., Mol. Micro., 19:1167–1175 (1996)), or the channels they use, with mutations such as tolC (Schnaitman et al., J. Bacteriol., 172(9):5511–5513, (1990)), also result in increased chemical sensitivity. In some instances, the target macromolecule of a chemical may be intrinsically resistant to the action of that chemical. For example, E. coli has two isozymes of the enzyme acetolactate synthase (ALS), one of which has a poor binding affinity for the sulfonylurea herbicides. Mutations which destroy the function of ilvBN, encoding the resistant isozyme, result in a strain with greatly increased susceptibility to growth inhibition by sulfonylurea herbicides that target acetolactate synthase (LaRossa and Smulski, *J. Bacteriol.*, 160:391–394 (1984)). An appropriate host strain of *E. coli* or other bacteria may be constructed to carry a known mutation or combinations of mutations. Furthermore, an appropriately sensitive strain may also be found by screening for growth inhibition following mutagenesis by transposon insertion or chemical or physical treatments.

The present invention further provides a transformed host cell capable of increased luminescence in the presence of a cellular insult. Many suitable hosts are available where *E. coli* is preferred and the *E. coli* strain DPD 1675 (ilvB2101 ara thi Δ(pro-lac) tolC::miniTn10) is most preferred. DPD1675 was derived by phage P1 mediated generalized transduction using a lysate grown on strain DE112 (strR, galK2, lac Δ74 tolC::miniTn10) as a donor and strain CU847 (ilvB2101 ara thi Δ(pro-lac)) as a recipient. Resultant tetracycline resistant transductants were screened for hypersensitivity to the hydrophobic compound crystal violet.

Cellular Stress—Cellular Insults

The present invention provides a method for the detection of bacterial regulatory elements responsive to a variety of cellular stresses (produced by cellular insults) such as those produced when a cell contacts chemicals , such as herbicides, crop protection chemicals, environmental pollutants, heavy metals, changes in temperature, changes in pH, agents producing oxidative damage, insults causing DNA damage, insults causing anaerobiosis, and biological insults such as the pathogenic life forms (viruses, bacteria, etc.). Preferred regulatory regions will be responsive to chemicals used in the agrochemical industry such as CPC's including herbicides. The regulatory regions identified include those responsive to sulfonylurea herbicides and sulfonanilide herbicides (chlorsulfuron, triasulfuron, metsulfuron-methyl) and glyphosate, phosphinothricin, asulam, and quizalofop. It is contemplated that regulatory regions responsive to other agrochemicals may also be identified by the present method including but not limited to pesticides (paraquat, copper sulfate, metidathion), anti-pathogenic compounds such as fungicides (chlorothalonil), chemicals responsible for insect behavior modulation (pheromones, allomones and kairomones), auxin herbicides (e.g. dicamba, 2-methyl-4-chlorophenoxyacetic acid, picloram, quinclorac, quinmerac), pre-emergence herbicides (metribuzin), and post-emergence herbicides (Clethodim Pendimethalin, oryzalin, dithiopyr, oxadiazon, prodiamine, 2-4-D).

Culture Conditions

Typically cells are grown at 37° C. in appropriate media. Preferred growth media in the present invention are common defined media such as Vogel-Bonner medium (Davis et al., *Advanced Bacterial Genetics* 1980, Cold Spring Harbor, N.Y.: Cold Spring Harbor Laboratory). Other defined or synthetic growth media may also be used and the appropriate medium for growth of the particular microorganism will be known by someone skilled in the art of microbiology or fermentation science.

Suitable pH ranges for bacterial growth are between pH 5.0 to pH 9.0, where pH 6.0 to pH 8.0 is preferred as the initial condition.

Growth of the bacterial cells in liquid medium allows a uniform population of cells to be stressed at various growth phases such as early log phase, mid log phase, late log phase or stationary phase. Stress is the condition produced in a cell as the result of exposure to a cellular insult. This cellular insult may be caused by any substance or change in the cellular environment that results in an alteration of normal cellular metabolism in a bacterial cell or population of cells. The addition of chemicals such as herbicides, crop protection chemicals, environmental pollutants, or heavy metals to the growth media can cause such an insult. Additionally, changes in temperature, changes in pH, agents producing oxidative damage or DNA damage (such as from UV exposure), anaerobiosis, or changes in nitrate availability may cause insult as well.

Identification of regulatory regions

Genomic segments containing regulatory regions responsive to an cellular insult are identified by screening for altered luminescence following application of the cellular insult to individual isolates of the transformed host cells containing random chromosomal DNA fragments. A genomic segment is identified as containing a regulatory region if its presence upstream of the reporter gene(s) results in increased or decreased activity of the reporter gene(s) after application of the cellular insult to cells containing the genetic fusion. The genomic segment present in a particular plasmid is identified by the sequence of the ends of the chromosomal DNA fragment. The regulatory region, therefore, is a genomic segment located between those ends. Smaller genomic segments within that originally defined region will also likely be sufficient to function as the regulatory region. These smaller segments are identified by the altered activity of a reporter gene(s) following application of the environmental insult to cells containing a genetic fusion of the regulatory region to a reporter gene(s). The regulatory region may also be identified as the region responsible for altered messenger RNA or protein synthesis from the stress gene following application of the environmental insult to cells.

The application of the invention to discovery of *E. coli* genomic segments containing regulatory regions responsive to the herbicide sulfometuron methyl and 2,4-dichlorophenoxyacetic acid are described in detail in the GENERAL METHODS and EXAMPLES. A number of previously unidentified regulatory regions were discovered. These regulatory regions are contained within the chromosomal DNA fragment cloned into the multiple cloning site of pDEW201. However, it is likely that smaller segments of chromosomal DNA would be sufficient to function as the regulatory region. These are identified as the genomic segment responsible for increased transcription of the stress gene, which may be quantitated by increased activity of a reporter gene(s) in a genetic fusion, increased messenger RNA synthesis or increased protein synthesis.

Genomic segments containing regulatory regions responsive to other chemicals are found by this method also. In particular, it is expected to be useful to discover such segments responsive to crop protection chemicals that are known to inhibit metabolic processes that are in common to bacteria and plants. These would include, but are not limited to, glyphosate, an inhibitor of ESPS synthase (5-enolpyruvyl-shikimicacid-3-phosphate synthase) (*Biochem. Biophys. Res. Commun.* 94:1207–12 (1980)), phosphinothricin, an inhibitor of glutamate synthase (Baron et al., *Plant Physiol. Biochem.* (Paris) (1994), 32(4):555–60), asulam (Kidd et al., *Plant Sci. Lett.* (1982), 26(2–3), 211–17), a folate biosynthesis inhibitor, and quizalofop-ethyl, an inhibitor of acetyl CoA carboxylase (Dehaye et al., *Eur. J. Biochem.* 225:1113–23 (1994).

Discussion of the Preferred Embodiments

Figure 2:
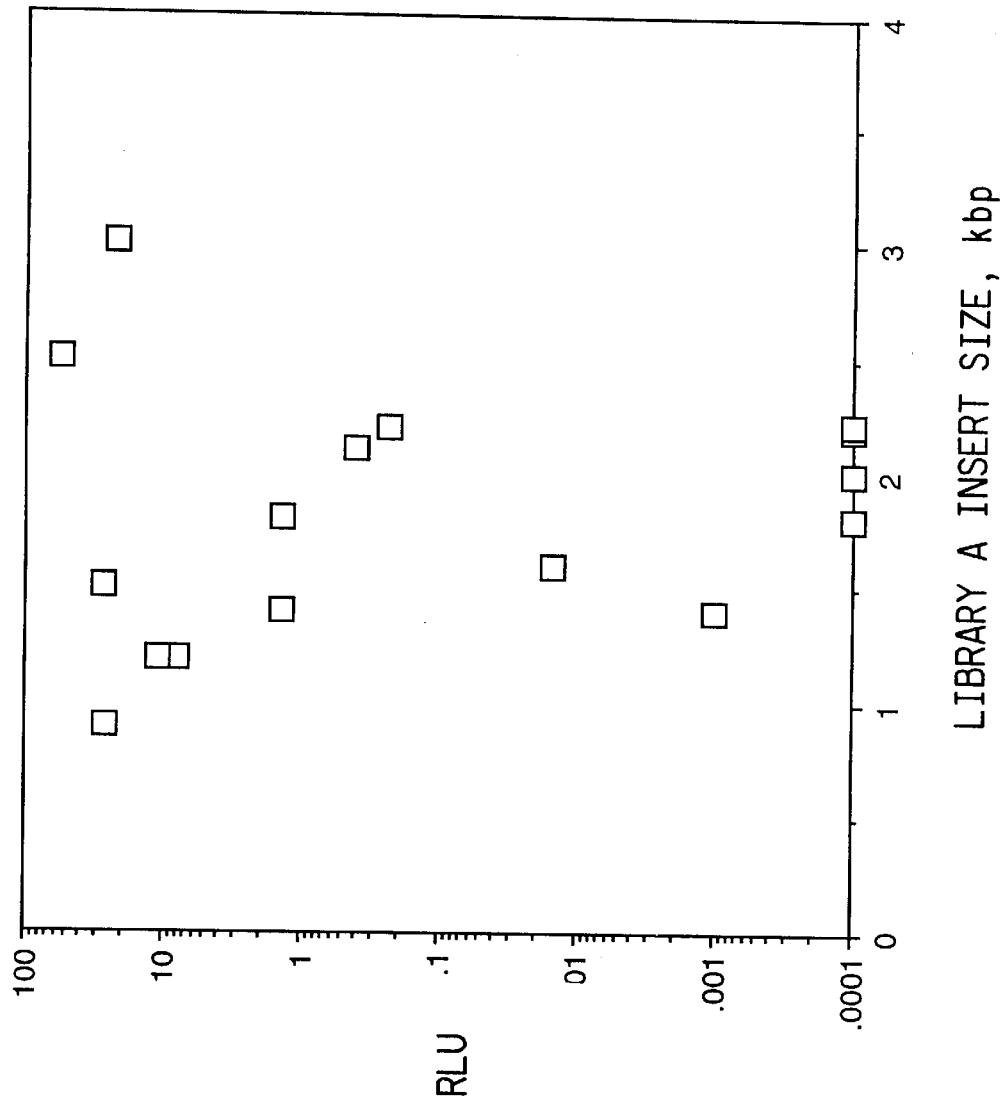
FIGS. 2 and 3 show graphically light production as a function of insert size for individual transformants of Library A and Library Z, respectively.
Figure 3:
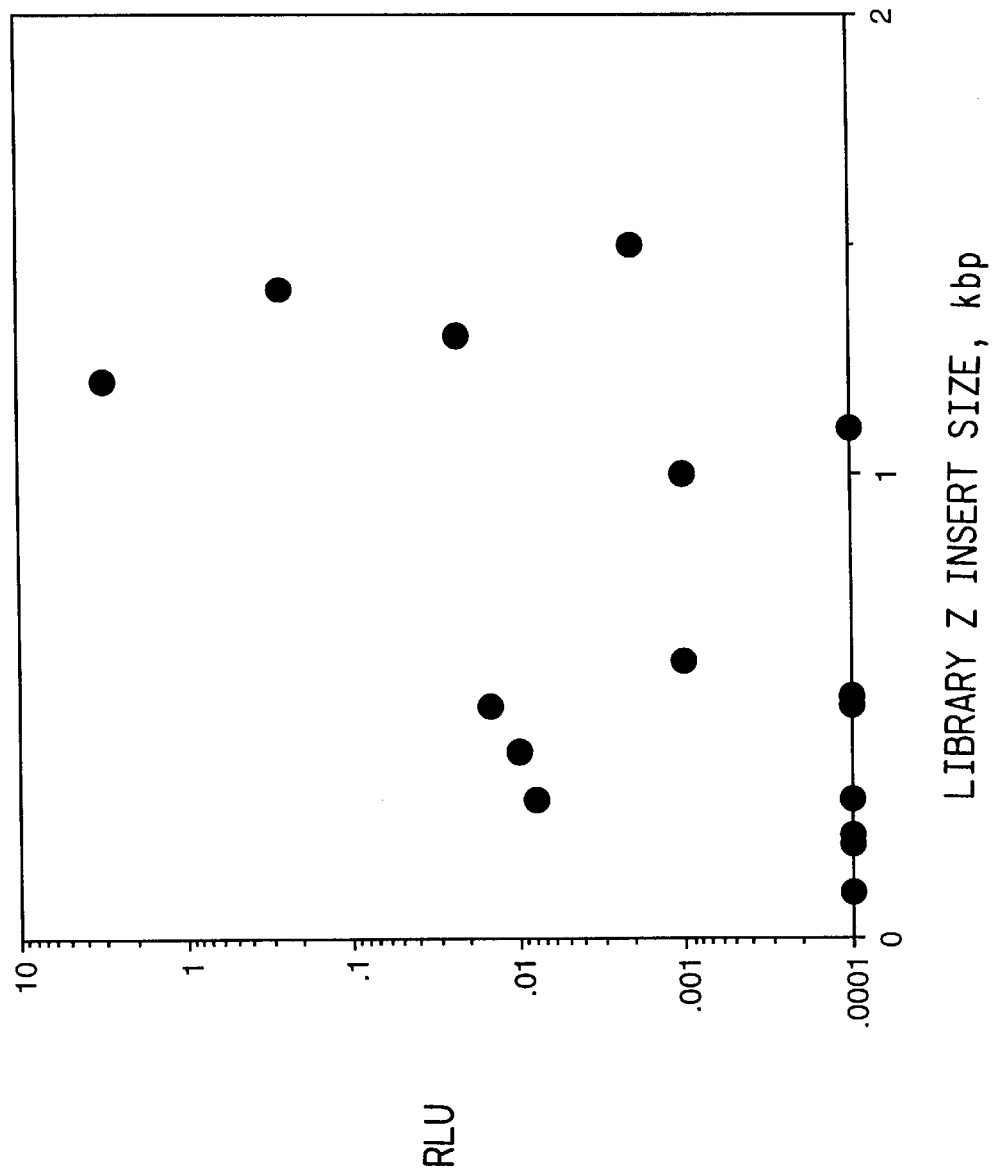
Figure 4:
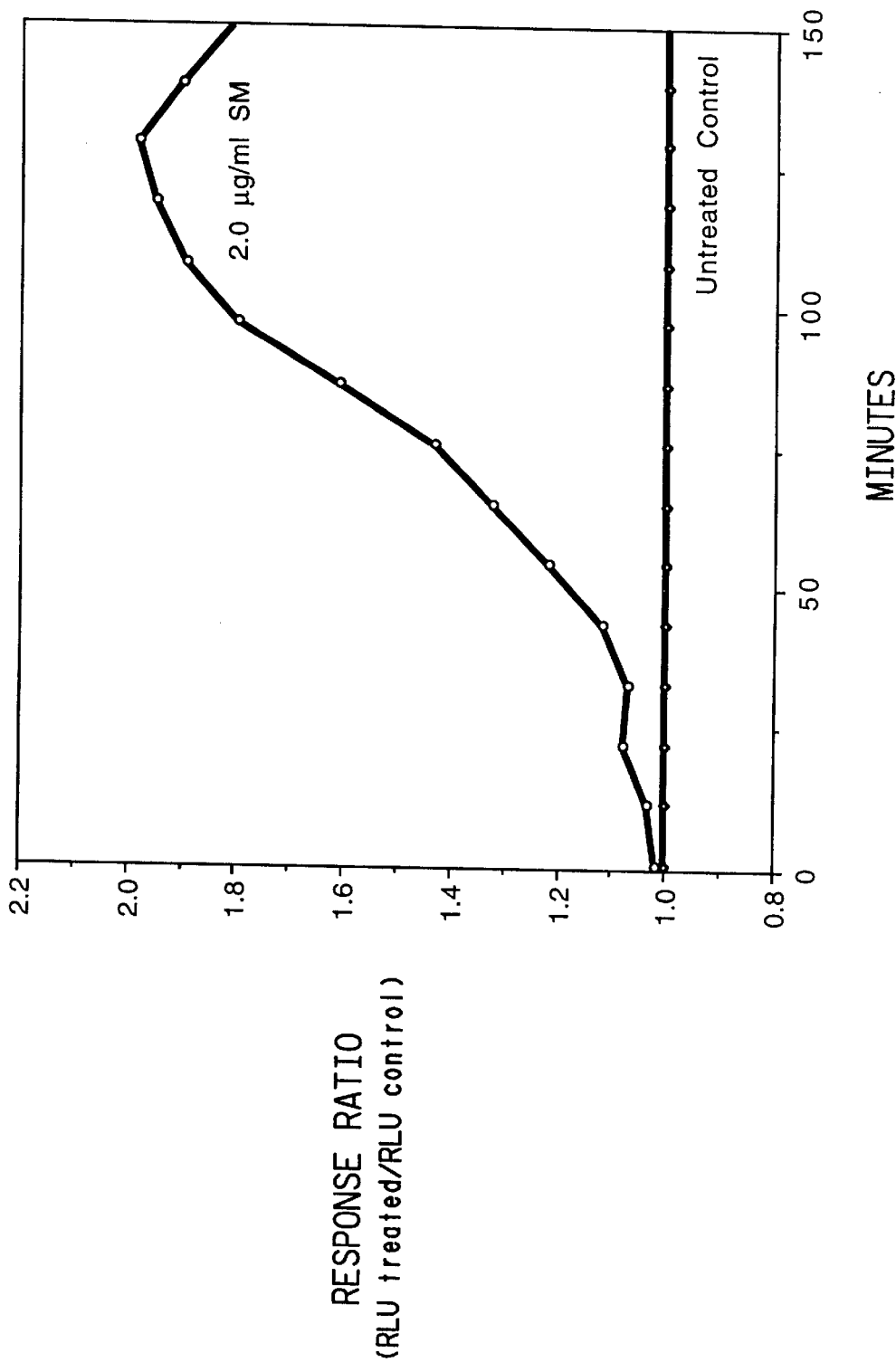
FIG. 4 shows graphically the induction of bioluminescence of transformant DPD2088 by sulfometuron methyl.
Figure 6:
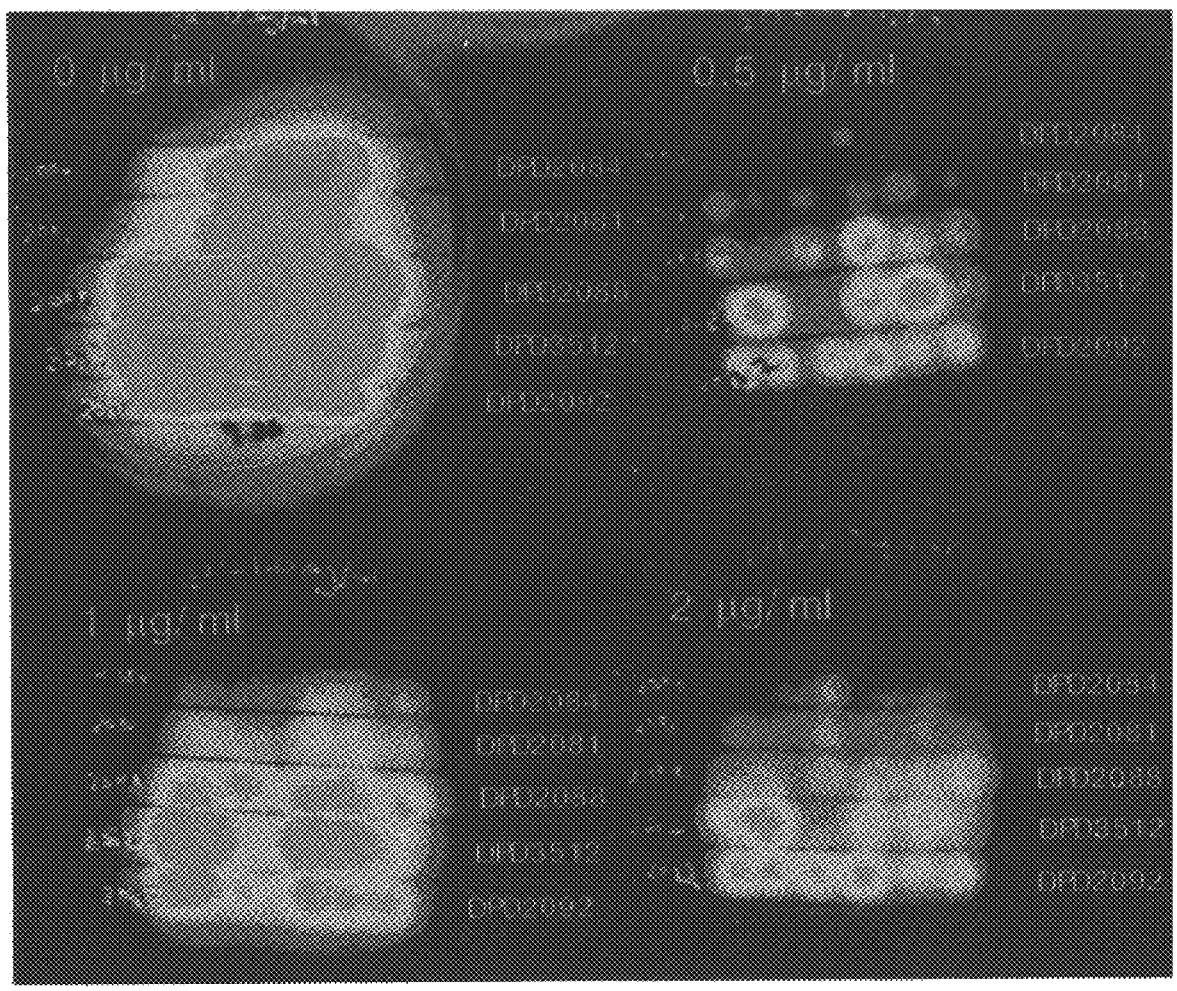
FIG. 6 is a color-enhanced, electronic image of an X-ray film comparing bioluminescence of transformants DPD2084, DPD2081, DPD2088, DPD3512, and DPD2092 that were cultured on plates with and without sulfometuron methyl induction.

The data shown in FIGS. 2 and 3 demonstrate a key feature of this method: promoters of a wide range of activity are readily detected and quantitated by the resultant light production. An advantage of this method is that promoters of varied activities may all be measured with the same conditions at the same time. Furthermore, the activity of collections of such promoters can be screened for changes following cellular stress. An example, the SM induction of a strain identified by this method, is shown in FIG. 4. It is not likely that this strain or others would have been identified by screening on plates, as typically done. This is shown in FIG. 6 where the bioluminescence of several strains identified by this method was recorded following growth on plates containing SM. Increases of bioluminescence on the SM-containing plates were not detected. This is may be in part because of the decreased amount of growth in the presence of the chemical. In fact, higher concentrations of SM ($\geq 3$ μg/mL) that were useful for characterizing fusion-containing strains in liquid medium could not be used on the plates because little to no growth resulted.

FIG. 6 shows another aspect of this invention. Various herbicidal chemicals were used to stress SM-inducible fusion containing strains identified by this method. A pattern of induction for each herbicidal chemical was observed. It was noted that two chemicals, SM and glyphosate, gave very similar patterns of induction. Thus, these fusion-containing strains may be useful as screens for compounds that will be effective herbicides. Furthermore, these fusion containing strains also may be useful for characterizing the modes of action of herbicides or potential herbicides.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES
GENERAL METHODS

Procedures for phosphorylations, ligations and transformations are well known in the art. Techniques suitable for use in the following examples may be found in Sambrook et al., *Molecular Cloning: A Laboratory Manual*, Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters, μL means microliters, and μg means micrograms.

EXAMPLE
1. Construction of a promoter probe vector

Plasmid pDEW201 was made by replacing the promoterless lacZ gene of pRS415 (Simons et al., *Gene*, 53:85–96 (1987)) with the promoterless *Photorhabdus luminescens* luxCDABE from pJT205 (Rosson, *PCT International Application* WO 93/03179, 57 pp., (1993)). Plasmid pRS415 contains an origin of replication from pBR322, a bla gene and four tandem transcription terminators from phage T1 upstream of a multiple cloning site (MCS). This plasmid DNA was digested with BamH I, Nru I and EcoR V and ligated with pJT205 DNA that had been digested with BamH I, Pvu II and Pst I. The ligation mixture was used to transform *E. coli* strain DH5, selecting for ampicillin resistance. Light production from overnight cultures of transformant colonies that had been grown in LB medium containing 150 μg/mL of ampicillin was quantitated in an ML3000 luminometer in the presence and absence of 0.0033% nonanal. Plasmid DNA was isolated from three transformants that had very low levels of light production (0.0022 to 0.0029 RLU) in the absence of nonanal and moderate light production (0.91 to 0.97 RLU) in the presence of nonanal. Restriction digestion analysis with various enzymes and combinations of enzymes showed that each of these three plasmids had the expected structure except that a portion (c.a. 900 bp) near the 3' terminus of the luxCDABE operon containing an EcoR I site was deleted. One of these plasmids was saved and named pDEW201. The entire luxCDABE operon is known to remain intact in pDEW201 because placement of DNA with promoter activity in the multiple cloning site results in light production in the absence of exogenously added aldehyde. Furthermore, DNA sequence analysis of the 3' region of the lux operon in pDEW201 showed that the join point of the sequences derived from pJT205 to sequences derived from pRS415 was one nucleotide beyond the termination codon of luxE.

A map of plasmid pDEW201 is shown in FIG. 1. Features of this plasmid include: (1) unique EcoR I, BamH I, Kpn I and Sac I sites in the multiple cloning site; (2) promoterless *Photorhabdus luminescence* luxCDABE genes downstream of the multiple cloning site; (3) transcription terminators upstream of the multiple cloning site resulting in a very low level of read-through transcription and hence very low light production in the absence of promoter DNA cloned into the multiple cloning site from cells containing this plasmid; (4) ampicillin resistance selection for maintenance of the plasmid; and (5) moderate copy number due to the replication origin from pBR322.

2. Construction of libraries

Chromosomal DNA isolated from *E. coli* W3110 was partially digested with restriction enzyme Sau3A1 and size fractionated on agarose gels. Fractions of three size ranges (average sizes of approximately 700, 1800 or 2500 basepairs) were ligated to pDEW201 that had previously been digested with restriction enzyme BamHI and treated with calf intestinal alkaline phosphatase. The ligation products were used to transform ultracompetent *E. coli* XL2Blue (Stratagene) to Amp$^R$ (ampicillin resistant). Pooled transformants were cryogenically preserved and used to isolate plasmid DNA.

3. Characterization of libraries of cloned random DNA upstream of lux

Single ampicillin resistant transformants of *E. coli* XL2Blue were toothpicked from transformation plate to wells of a white microtiter plate containing 100 μl of LB medium (Miller, *Experiments in Molecular Genetics*, 1972, Cold Spring Harbor, N.Y.: Cold Spring Harbor Laboratory). Light production was quantitated in an ML 3000 luminometer and compared with control pDEW201 transformants. Those with greater light production than the control were scored Lux$^+$. The results are shown in Table I.

TABLE I

| Library | approx. size of inserted DNA | #Lux+/total picked | % Lux+ |
|---|---|---|---|
| Z | 500–2000 | 21/88 | 24% |
| A | 900–3000 | 49/88 | 56% |
| B | 1500–4500 | 60/88 | 68% |

As expected, there were a greater percentage of cloned fragments with promoter activity, hence light production, as the size of inserted DNA was increased.

Light production and insert size from 16 random individual transformants of libraries A and Z grown overnight in LB medium containing 150 μg/mL ampicillin was characterized. Bioluminescence from two 100 μL samples was quantitated, averaged and compared with the bioluminescence of pDEW201 transformants. The remaining 4.8 mL of the overnight culture was used to isolated plasmid DNA, which was subsequently digested with restriction enzymes EcoRI and SacI to release the fragment inserted into the MCS. Table II below summarizes the findings.

TABLE II

| Library | Lux+/total | range of RLU | Insert+/total | Insert size range, kbp | Avg. insert size |
|---|---|---|---|---|---|
| Z | 9/16 (56%) | 0.001–3.0 | 16/16 (100%) | 0.1–1.5 | 0.7 kbp |
| A | 11/16 (69%) | 0.015–27 | 16/16 (100%) | 0.9–3.0 | 1.8 kbp |

FIGS. 2 and 3 display the light production as a function of insert size for these transformants. The large range of light production indicates that promoters of many strengths are present in the libraries. Furthermore, it demonstrates the advantages of the large dynamic range of the lux reporter in that these varied plasmids containing promoters of varied activities could all be measured with the same conditions at the same time.

4. Identification of appropriate *E. coli* host strains

To discover the effects of chemicals on the cell without presupposition concerning the nature of those effects, the host strain should be as close to wild type as possible. Nevertheless, certain features are important. In order for the growth of *E. coli* to be inhibited by the sulfonylureas, such as sulfometuron methyl (SM), the SM-resistant ALS I must be eliminated by an ilvB⁻ mutation. Another desirable feature is increased sensitivity to chemicals. *E. coli* strains mutated in tolC lack the outer membrane channel for an hydrophobic compound efflux pump and thus are sensitive to growth inhibition at reduced chemical concentrations. The *E. coli* strain DPD 1675 [ilvB2101 ara thi Δ(pro-lac) tolC::miniTn10], has both an ilvB⁻ mutation and a tolC⁻ mutation with few other mutations.

5. Screening for SM-inducible promoters

Plasmid library A was used to obtain AmpR transformants of *E. coli* DPD1675. These transformants, each of which contained random, individual plasmids with *E. coli* DNA fused to the lux reporter, were toothpicked to wells of a microtiter plate. Each well contained 100 μL of Vogel-Bonner (Davis et al., *Advanced Bacterial Genetics*, (1980), Cold Spring Harbor, N.Y.: Cold Spring Harbor Laboratory) with glucose as a carbon source and supplemented with thiamine, uracil, proline and 25 μg/mL ampicillin. Following overnight growth at 37° C., these pure cultures were used for both permanent storage (Menzel, *Anal. Biochem.*, 181:40–50 (1989)) and dilution and regrowth to exponential phase in the same medium except containing 10 μg/mL ampicillin. These actively growing cultures were tested for the effects of SM addition by adding 50 μL to 50 μL of fresh medium lacking ampicillin but containing 4 μg/mL SM (E. I. du Pont de Nemours, Wilmington, Del.). The final SM concentration, 2 μg/mL, resulted in partial (25%) inhibition of *E. coli* DPD1675 growth rate. Light production was quantitated in a ML3000 luminometer at 0, 90, and 180 min of incubation at 37° C. after addition of cell cultures to chemical. The criteria of Table III were used to identify putative SM-inducible fusions.

TABLE III

| RLU (SM treated) - RLU (control) | | RLU (SM treated)/RLU (control) |
|---|---|---|
| ΔRLU | 0.02 → 0.1 | Ratio ≥ 1.50 |
| ΔRLU | 0.1 → 1.0 | Ratio ≥ 1.35 |
| ΔRLU | 1.0 → 10.0 | Ratio ≥ 1.25 |
| ΔRLU | >10.0 | Ratio ≥ 1.20 |

Putative transformants were reisolated from the appropriate wells of the duplicate cultures stored at −80° C. and retested under the same conditions as above. Those that showed SM-induced increased bioluminescence in the second test were tested at third time at a variety of SM concentrations and for a longer extent of time. An example of induction of bioluminescence from one of these fusions is shown in FIG. 6. Strains that continued to show good SM induction were selected for further analysis including DNA sequencing to identify the inserted DNA in the plasmid. Of the 8066 random fusion containing transformants that were screened, twenty were selected for DNA sequence analysis.

6. DNA sequence analysis

The DNA sequence information from both ends of the inserted DNA was analyzed by comparison with the *E. coli* chromosomal sequence using the ECDC database (Kröger and Wahl, *Nucleic Acids Res.*:24:29–31 (1996)). A summary of the identities of the twenty inducible fusions is shown in Table IV. In all cases where the sequence was identified, the promoter closest to the lux reporter genes was situated such that the transcription initiated at that promoter would drive lux expression. The 17 single insert fusions represent 13 unique fusions of DNA with promoter activity to luxCDABE.

Sequence data was obtained by automated DNA sequencing. For those sequences labeled "upper" the primer, GGATCGGAATTCCCGGGGAT (SEQ ID NO: 27), from just upsteam of the MCS of pDEW201 was used. For those sequences labeled "lower", the primer, CTGGCCGT-TAATAATGAATG (SEQ ID NO: 28), from the luxC region of pDEW201 was used. The sequences listed are those used for comparison with the *E. coli* sequence database. For the upper sequences, it starts about 30 bases into the sequence and continues to the first ambiguous base (N). For the lower sequences, it starts immediately after the BamHI site and continues to the first ambiguous base (N). In some cases, a few ambiguous bases (N) may be included. All sequences are shown 5' to 3'.

TABLE IV

DNA Sequence Analyis of 20 SM-Inducible Genes

| Total | Subfusions | Categories | | Other Information |
|---|---|---|---|---|
| 3 | — | Double insert => No further analysis (3 of 3 fusions) | | |
| 3 | — | No hits to database (3 of 3 fusions) Unique (1 of 3 fusions) Identical to each other (2 of 3 fusions) | | |
| 4 | — | Hit at one end only (4 of 4 fusions) (upper primer sequence) 51.49 min (1 of 4 fusion) 52.31 min (3 or 4 fusions) | | Downstream of ack Downstream of glk |
| | 6 "unknown" orfs | | | |
| | 1 ldcH | | 4.5 min | Predicted function: lysine decarboxylase |
| | 1 yciG | | 28.2 min | Predicted function: unknown |
| | 2 yohF | | 47.4 min | Predicted function: dehydrogenase |
| | 1 yiaB | | 80.3 min | Predicted function: unknown |
| | 1 frvX | | 88.1 min | Predicted function: unknown. |
| | 4 known genes | | | |
| | 1 poxB | | 19.6 min | Pyruvate oxidase Regulated by rpoS |
| | 1 inaA | | 50.0 min | Function: not known Induced by acid shock and other environmental insults Regulated by soxRS and mar |
| | 1 sohA | | 70.6 min a.k.a. prlF | Activation of the Lon protease Auto regulated |
| | 1 osmY | | 99.3 min | Periplasmic protein induced by hyperosmotic insult Regulated by rpoS, lrp, cAMP, and IHF |

7. Functional grouping of fusion containing strains

Each of the 13 unique single insert fusion strains was characterized by testing actively growing cells in Vogel-Bonner medium with glucose as the carbon source supplemented with thiamine, proline and uracil challenged with final concentration of chemicals: 3 or 8 $\mu$g/mL SM or 5 mM salicylate, a weak, membrane-permeant acid. Bioluminescence was quantitated for >1000 min in an ML3000 luminometer at 37° C. in plates covered with acetate seals. Data from plots of RLU vs. time were analyzed calculating "very early" induction ratios and "peak" response ratios. The ratio of the RLU from treated samples (with SM 3 $\mu$g/mL or Salicylate 5 mM) at the 90 min time point to the control RLU at the 90 min time point was the "very early" induction ratio; the fusion was considered induced if this ratio was >1.3. The ratio of the peak RLU of treated cells (with SM 8 $\mu$g/mL or Salicylate 5 mM) at any time point in the experiment to the peak RLU at any time point of the control cells was the "peak" response ratio; the fusion was considered induced if this ratio was >1.5. Also calculated was the ratio of the RLU peak of the untreated cells to the RLU of the untreated cells at the second cycle (1000 sec) of the experiment. Table V shows the classes of fusions from this data.

TABLE V

Classes of fusion strains

"Class 1" Stationary phase inducible (and putatives)

| Strain | Fusion | SM induction RLU (SM)/ RLU control | Salicylate induction RLU (Sal.)/ RLU control | Overnight peak/initial RLU (second cycle) | Genomic Segment bounded by SEQ ID NOS: |
|---|---|---|---|---|---|
| DPD3509 | poxB'::lux (pyruvate oxidase) | Very early only: 1.9/1.3 = 1.5X | Very early only: 2.9/1.3 = 2.2X | 17/0.5 = 34X | 23 and 24 |
| DPD2090 | osmY'::lux (outer membrane protein) | Very early only: 0.12/0.08 = 1.5X | Very early only: 0.12/0.08 = 1.5X | 1.6/0.05 = 32X | 13 and 14 |

TABLE V-continued

Classes of fusion strains

| DPD2088 | yohF'::lux (putative dehydrogenase) | Very early: 0.6/0.3 = 2X Late (slight): 7.4/4.3 = 1.7X | Very early only: 0.6/0.3 = 2X | 4.3/0.2 = 22X | 9 and 10 |
|---|---|---|---|---|---|
| DPD3505 | unmapped (no clues from protein database) | Very early only: 1.1/0.7 = 1.6X | Not induced | 7.2/0.35 = 21X | 19 and 20 |

"Class 2" Acid inducible (and putatives)

| Strain | Fusion | SM induction | Salicylate induction | Overnight peak/initial RLU (second cycle) | Genomic Segment bounded by SEQ ID NOS: |
|---|---|---|---|---|---|
| DPD2087 | inaA'::lux (acid inducible, unknown func.) | Moderate late: 200/90 = 2.2X | Very early (strong): 130/25 = 5.2X Late: 325/90 = 3.6X | 90/10 = 9X | 7 and 8 |
| DPD3507 | sohA'::lux (Lon activator) | Moderate late: 160/80 = 2X | Very early: 42/22 = 1.9X Late (Slight): 155/80 = 1.9X | 80/10.5 = 7.6X | 21 and 22 |
| DPD3501 | frvX'::lux (unknown function) | Moderate late: 24/10 = 2.4X | Very early: 4/2.6 = 1.5X Late (Slight): 17.5/10 = 1.8X | 10/1.2 = 8.3X | 17 and 18 |
| DPD2089 | unmapped (no clues from protein database) | Very early: 11.0/7.5 = 1.5X Moderate late: 55/18 = 3.1X | Very early: 19.5/7.5 = 2.6X Late (Slight): 30/18 = 1.7X | 18/6 = 3X | 11 and 12 |
| DPD3512 | ldcH'::lux (putative lysine decarboxylase) | Very early: 1.2/0.6 = 2X Moderate late: 10.2/2.5 = 4.1X | Very early: 1.05/0.6 = 1.8X Late (Slight): 4.5/2.5 = 1.8X | 2.5/0.38 = 6.6X | 25 and 26 |

"Class 3" Stationary phase (very strong) and acid inducible (putative)

| Strain | Fusion | SM induction | Salicylate induction | Overnight peak/initial RLU (second cycle) | Genomic Segment bounded by SEQ ID NOS: |
|---|---|---|---|---|---|
| DPD2092 | downst. of ack (putative transmembrane protein) | Very early: 0.99/0.72 = 1.4X Late: 130/15 = 8.7X | Late only: 50/15 = 3.3X | 15/0.06 = 250 | 15 and 16 |

"Class 4" Possible SM-specific induction

| Strain | Fusion | SM induction | Salicylate induction | Overnight peak/initial RLU (second cycle) | Genomic Segment bounded by SEQ ID NOS: |
|---|---|---|---|---|---|
| DPD2084 | yciG'::lux (unknown function) | Very early: 0.18/0.11 = 1.6X Moderate late: 1.5/0.7 = 2.1X | Not induced | 0.7/0.09 = 7.8X | 3 and 4 |
| DPD2086 | yiaB'::lux (unknown function) | Very early only (v. slight): 0.17/0.15 = 1.1X | Not induced | 0.45/0.085 = 5.3X | 5 and 6 |

"Class 5" Generally inducible by many stresses

| Strain | Fusion | SM induction | Salicylate induction | Overnight peak/initial RLU (second cycle) | Genomic Segment bounded by SEQ ID NOS: |
|---|---|---|---|---|---|
| DPD2081 | downst of glk (putative fructose specific iic component of pts) | Very early: 0.5/0.2 = 2.5X Late: 3.6/.35 = 10.3X | Early: 0.35/0.2 = 1.8X Late: 1.5/0.35 = 4.3X | 0.35/0.2 = 1.8X | 1 and 2 |

TABLE V-continued

Classes of fusion strains

"Control" Non-SM inducible, heat shock promoter

| Strain | Fusion | SM induction | Salicylate induction | Overnight peak/initial RLU (second cycle) |
|---|---|---|---|---|
| DPD2077 | grpE'::lux | None | Very early: 250/80 = 3.1X Moderate late: 700/340 = 2.1X | 340/48 = 7.1X |

8. Induction by other herbicides

Representative fusions from some of the classes above were tested for induction by other herbicidal compounds. Strains DPD3509 (poxB'::luxCDABE), DPD2087 (inaA'::lux), and DPD2081 (map position of fusion is downstream of glk) were grown in Vogel-Bonner medium with glucose as the carbon source supplemented with thiamine, proline and uracil until mid-log phase. These cultures were challenged with SM, glyphosate (Sigma, St. Louis, Mo.), phosphinothricin, asulam, or quizalofop-ethyl (Chem Services, West Chester, Pa. 19381). Bioluminescence was quantitated for >1000 min in an ML3000 luminometer at 37° C. in plates covered with acetate seals. Data from plots of RLU vs. time were analyzed calculating "early" and "peak" responses. The difference of the RLU from treated samples (SM 8 µg/mL, glyphosate 100 µg/mL, phosphinothricin 200 µg/mL, asulam 50 µg/mL or quizalofop-ethyl 50 µg/mL) at the 200 min time point from the control RLU at the 200 min time point was normalized by dividing by the RLU of the control sample at that time point to give the "early" response:

$$\frac{RLU(\text{treated, 200 min}) - RLU(\text{control, 200 min})}{RLU(\text{treated, 200 min})}$$

The difference of the peak RLU of treated cells (SM 16 µg/mL, glyphosate 100 µg/mL, phosphinothricin 200 µ/mL, asulam 50 µg/mL or quizalofop-ethyl 50 µg/mL) at any time point in the experiment to the peak RLU at any time point of the control cells was normalized by dividing by the peak RLU of the control sample to give the "peak" response:

$$\frac{RLU(\text{treated, peak}) - RLU(\text{control, peak})}{RLU(\text{treated, peak})}$$

Figure 5:
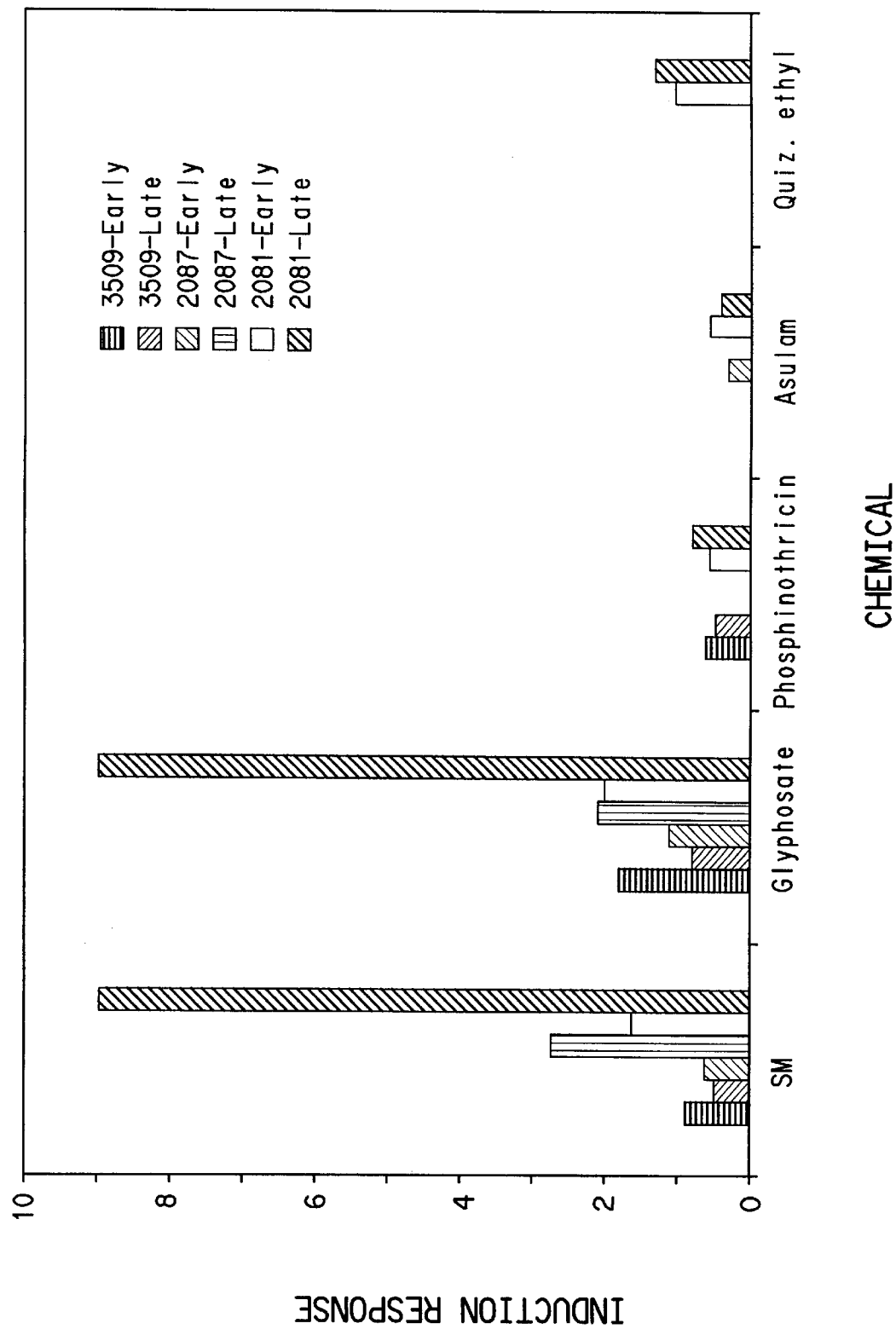
FIG. 5 shows graphically patterns of bioluminescence induction in transformants DPD3509, DPD2087, and DPD2081 by various herbicidal compounds.

FIG. 5 displays the results of these calculations; values less than zero are not shown. Each herbicide gives a pattern of induction of these three fusions that is unique. However, the similarity of pattern between SM and glyphosate is noted.

9. Bioluminescence detection on plates

The described method of discovery of promoters by inducing stress in cells growing in liquid medium is more sensitive than assessing activity of the reporter genes on petri plates. This was shown by testing several of the SM-induced fusion containing strains. E. coli strains DPD2084, DPD2081, DPD2088, DPD3512, and DPD2092 were streaked for single colonies on Vogel-Bonner medium agar plates with glucose as the carbon source and supplemented with thiamine, proline, uracil and ampicillin (25 µg/mL). Six single colonies of each were transferred with a toothpick to the plates of the same composition except lacking ampicillin and containing SM at 2 µg/mL, 1 µg/mL, 0.5 µg/mL or 0 µg/mL. Following incubation at 37° C. overnight, there was visible growth on all plates; however, the growth on the plates containing SM was visibly less dense. These plates were exposed to X-ray film (DuPont REFLECTIONS, Wilmington, Del.) at 37° C. for two h. The film was developed and examined visually. There was no increase in darkening of the film for any of these five strains on the plates with SM compared with those plates lacking SM. An image of the exposed and developed X-ray film was made by illuminating it on a light box, capturing an electronic image using the Eagle Eye™ II (Stratagene) system. Colors corresponding to the various exposures of the film were added to the image using a MACINTOSH QUADRA 800 computer and the public domain NIH Image program (written by Wayne Rasband at the U.S. National Institutes of Health and available from the Internet by anonymous ftp from zippy.nimh.nih.gov or on floppy disk from NTIS, 5285 Port Royal Rd., Springfield, Va. 22161, part number PB93–504868). These version of the relative bioluminescence of these E. coli strains grown on plates is shown in FIG. 6. As with visual examination of the film, there is no evidence of increased bioluminescence on the plates with SM compared with those plates lacking SM. Thus, it is unlikely that any of these five strains would have been scored SM-inducible by a plate assay.

10. Identification of regulatory regions responsive to 2,4-dichlorophenoxyacetic acid This method is also useful for discovery of regulatory regions modulated by other chemicals. This was shown by identification of fusion-containing strains showing bioluminescence which was inducible by the herbicidal compound 2,4-Dichlorophenoxyacetic acid. Plasmid libraries Z, A, and B were used to obtain ampicillin resistant transformants of E. coli DPD1675. These transformants, each of which contained random, individual plasmids with E. coli DNA fused to the lux reporter, were grown in wells of a microtiter plate. Each well contained 100 µL of Vogel-Bonner medium (Davis et al., Advanced Bacterial Genetics, (1980), Cold Spring Harbor, N.Y.: Cold Spring Harbor Laboratory) with glucose as a carbon source and supplemented with thiamine, uracil, proline and 25 µg/mL ampicillin. Following overnight growth at 37° C., these pure cultures were used for dilution and regrowth to exponential phase in the same medium except containing 10 µg/mL ampicillin. These actively growing cultures were tested by adding 50 µl to 50 µL of fresh medium lacking ampicillin but containing 100 µg/mL 2,4-Dichlorophenoxyacetic acid (Janssen Chimica). The final 2,4-Dichlorophenoxyacetic acid concentration was 50 µg/mL. Light production was quantitated in a ML3000 luminometer at 0, 1, 2, and 3 hours of incubation at 37° C. after addition of cell cultures to chemical. Eighty-eight transformants from each library (Z, A, and B) were tested. The Ratio of RLU in the treated sample to RLU in the untreated sample was calculated, as was the difference in RLU of the treated sample from the untreated. Fusion-containing strains which gave a ratio greater than or equal to 1.2 and an increase in RLU greater than 0.1 were scored as 2,4-Dichlorophenoxyacetic acid-inducible. Table VI list the results of 2,4-Dichlorophenoxyacetic acid-inducible isolated identified.

TABLE VI

| Gene fusion Library | Isolate # | Time of Treatment | Ratio | Increase in RLU |
|---|---|---|---|---|
| Z | Z1-C4 | 1 h | 2.1 | 2.5 |
|  | Z1-E11 | 1 h | 1.2 | 2.0 |
|  | Z1-C11 | 2 h | 1.5 | 0.3 |
| A | A1-H2 | 1 h | 1.3 | 25.2 |
|  | A1-F7 | 1 h | 1.2 | 4.5 |
| B | B1-D3 | 2 h | 1.3 | 23.9 |
|  | B1-A8 | 3 h | 1.3 | 0.3 |
|  | B1-E8 | 3 h | 1.7 | 14.1 |
|  | B1-F9 | 2 h | 1.4 | 1.8 |

We claim:

1. A method for identifying regulatory regions modulated by a cellular insult comprising:

(i) creating a library of gene fusions of genomic DNA fused to a promoterless, luminescent reporter gene complex selected from the group consisting of a gene complex encoding luciferase from Renella species, a thermostable lux gene complex, and a luxCDABE gene complex in Enteric bacteria to create fusion-containing strains;

(ii) culturing individual gene fusion-containing strains in liquid media;

(iii) contacting the fusion-containing strains at a particular growth phase with a cellular insult; and (iv) analyzing the fusion-containing strain for a change in luminescence relative to a baseline luminescence, said change in luminescence indicating that the fusion-containing strain includes a regulatory region modulated by the cellular insult.

2. The method of claim 1 further comprising recovering the fusion-containing strains containing a regulatory region modulated by the cellular insult.

3. The method of claim 1 wherein creating a library of gene fusions at step (i) is accomplished using a method of primer directed amplification, a method of restriction digestion, or a method of in vivo transposition.

4. The method of claim 3 wherein said a method of primer directed amplification is selected from the group consisting of Polymerase Chain Reaction, Ligase Chain Reaction, and Strand Displacement Amplification.

5. The method of claim 1 wherein said cellular insult is a chemical compound, a biological insult, or a physical treatment.

6. The method of claim 5 wherein said cellular insult is a crop protection chemical compound.

7. The method of claim 6 wherein the crop protection chemical compound is a N-(heterocyclicaminocarbonyl) sulfonamide-containing herbicidal chemical compound.

8. The method of claim 7 wherein the N-(heterocyclicaminocarbonyl) sulfonamide-containing herbicidal chemical compound is sulfometuron methyl.

9. The method of claim 1 wherein the fusion-containing strain is sensitive to at least one crop protection chemical compound.

10. The method of claim 9 wherein the at least one crop protection chemical inhibits acetolactate synthase (ALS), ESPS synthase, glutamate synthase, folate biosynthesis, or acetyl CoA carboxylase.

11. A method for identifying regularly regions modulated by a cellular insult comprising:

(i) creating a library of gene fusions of genomic DNA to a luminescent reporter gene complex in E. coli to create fusion-containing strains;

(ii) culturing individual gene fusion-containing strains in liquid media;

(iii) contacting the fusion-containing strain at a particular growth phase with a cellular insult for which the fusion-containing strain is known to be sensitive; and (iv) analyzing the fusion-containing strain for a change in luminescence relative to a baseline luminescence, said change in luminescence indicating that the regulatory region is modulated by the cellular insult.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: DPD2081 upper (xi) SEQUENCE DESCRIPTION: SEQ ID NO:1:

```
TTTGGTGGCG CAGAACCGGT CGAAGGTAAG CCTATTGCGG TTTACGGTGC CGGAACGGGG      60
CTTGGGGTTG CGCATCTGGT CCATGTCGAT AAGCGTTGGG TAAGCTTGCC AGGCGAAGGC     120
GGTCACGTTG ATTTTGCGCC GAATAGTGAA                                      150
```

(2) INFORMATION FOR SEQ ID NO:2:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2081 lower (xi) SEQUENCE DESCRIPTION: SEQ ID NO:2:

```
CCCATTGCGT ACATCAGCGC GCCCTTCTCA CCTGCGGCAG TCAGCACAGT ACGGATACCG      60
CCGTTGATCC AGCCACCAAA GGGGGTGATG ACGTA                                95
```

(2) INFORMATION FOR SEQ ID NO:3:

(i) SEQUENCE CHARACTERISTICS:
        (A) LENGTH:  414 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  dpd2084 upper (xi) SEQUENCE DESCRIPTION:  SEQ ID NO:3:

ATTCAAAACG CCACTCTGCG CGCCTTTGCG GCAGGTGTGA CTCCGGCACA ATGTTTTGAA        60

ATGCTGGCAC TGATTCGCCA GAAACACCCG ACCATTCCCA TTGGCCTGTT GATGTATGCC       120

AATCTGGTGT TTAACAAAGG CATTGATGAG TTTTATGCCC AGTGCGAAAA AGTCGGCGTC       180

GATTCGGTGC TGGTTGCCGA TGTGCCAGTT GAAGAGTCCG CGCCCTTCCG CCAGGCCGCG       240

TTGCGTCATA ATGTCGCACC TATCTTCATC TGCCCGCCAA ATGCCGATGA CGACCTGCTG       300

CGCCAGATAG CCTCTTACGG TCGTGGTTAC ACCTATTTGC TGTCACGAGC AGGCGTGACC       360

GGCGCAGAAA ACCGCGCCGC GTTACCCTCA ATCATCTGGT TGCGAACTGA AAGA            414

(2) INFORMATION FOR SEQ ID NO:4:

(i) SEQUENCE CHARACTERISTICS:
        (A) LENGTH:  283 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  dpd2084 lower (xi) SEQUENCE DESCRIPTION:  SEQ ID NO:4:

ATTTTTAAAA TTACCGCCGC TATGCTGACC GCCTTTACGG CCTGCGTCGG ATGCCTTCTC        60

ACGGTCTTCG GCGAAATTTC CTGAACCACC ACGATGTTCG GCCATGTTAT TTCTCCCGTT       120

GCGTTGCATT GTTTCATTAA TATGAGTGTT GTGTGTCGAC ACTCATTAAA ATTAGTCGCT       180

AATGAGAATT AGTCAAATTA AGCGCAACGA AAGATAGAG GGAAAATATA TTTTGAGGAA        240

CATTCTGGAT ATATTAACAA TTACCTGAGG AATAAGTGAC TTA                        283

(2) INFORMATION FOR SEQ ID NO:5:

(i) SEQUENCE CHARACTERISTICS:
        (A) LENGTH:  185 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  dpd2086 upper (xi) SEQUENCE DESCRIPTION:  SEQ ID NO:5:

CGCGATGGAT ACGATGGCAC TGGCGCTGAA ATTGCGCGCG CATGATTGAA ATGGCAAGCT        60

GGAAAACGCA TCGCGCACGT TATTCCGGCA TGGAATAACG AATTGGGCCA CCAAATCCGA       120

AAGGCCGGTG TCACTGGCAA TTTAGCCAAA TATGCTCAGG AACATCATGT GTCTCCGGTG       180

CATCA                                                                   185

(2) INFORMATION FOR SEQ ID NO:6:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2086 lower (xi) SEQUENCE DESCRIPTION: SEQ ID NO:6:

```
TCCATATCTA CCAGCGATAC ATTACGAGTA ACCAACGAAA GACAAAACTG AAAAATGCCA    60

TTAACAAATG ATTTTCAGAA TAAATTCATA CTAAATATTA ATTAATTACT GAGATATATA   120

GATGTGAATT ATCCCCCACC CGGTCAGGCA GGGGATAACG TTTACGCCAT TAATGGCAGA   180

AGTTGCTGAT AGAGGCGACG GAACGTTTCT CGTCGTGGCT GATAAGCGGC ATAACGCTGC   240

GCATCTGGTA GATGCGACTG TTCTAACGGT AGTTGCGGCA ACAATTCAAT GAGCGATTTC   300

TCTGGATTCG CCGCGATCTG CGCCAGCCTT GCTGCGCCCA GTGCTGGCCC CACATCCCCC   360

CCCGTACGGT AATCGAGCTG CTGACCGCTG ATATCCGCCA GCATCTGACG CCAGTACTCA   420

CTACGCGCCC CGCCCCCAAT CAACGTAACA CTTTGCGGTT AATACCGCA GGCATGCAC    479
```

(2) INFORMATION FOR SEQ ID NO:7:

(i) SEQUENCE CHARACTERISTICS:
        (A) LENGTH: 533 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2087 upper (xi) SEQUENCE DESCRIPTION: SEQ ID NO:7:

```
TCGTTACTAC GCGATAGATT TCACGCTGGA TGAAATTAAG TCGTTGAAAT TTACCGAAGG    60

TTTCGATATT GAAAACGGTA AAAAGTGCA GACTTATCCG GGGCGTTTCC CAATGGGTAA    120

GTCCGACTTC CGGGTGCACA CCTTTGAAAA AGAGATTGAA TTTGTTCAGG GGTTAAATCA   180

CTCTACCGGG AAAAATATCG GTATTTATCC AGAAATCAAA GCGCCGTGGT TCCATCATCA   240

GGAAGGGAAG GATATTGCGG CAAAAACGCT GGAAGTGCTG AAGAAATATG GTTACACCGG   300

TAAAGACGAT AAAGTTTATT TGCAATGTTT TGATGCTGAT GAGCTGAACG TATTAAGAAT   360

GAGCTGGAAC CCAAAATGGG CATGGAGCTC AATCTGGTAC AGCTGATTGC CTATACCGAC   420

TGGAATGAAA CGCAGCAGAA ACAGCCGGAT GGAACTGGGT TAATTACACT ACGACTGGAT   480

GTTTAACCGG GTGCCATGAA ACAGGTGGCG GAATATGCAG ATGGTATTGG TCC          533
```

(2) INFORMATION FOR SEQ ID NO:8:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2087 lower (xi) SEQUENCE DESCRIPTION: SEQ ID NO:8:

```
TTCGGCACGA TGACACCGGC CCGTTCCAGT TCTTTAATTA CCGCAACCTC ACGGACAATC      60

GTTGGTCGGC CGAACGGATA ACGTACGGAA TGAAACAGAT GATGCGTCAT GCGCTTTACA     120

TACAGCTTTT TGCCGTTGCG CTCGACGCAT TGCACCCCGC TCATACCATT ACGGCGATAG     180

TTA                                                                  183
```

(2) INFORMATION FOR SEQ ID NO:9:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2088 upper (xi) SEQUENCE DESCRIPTION: SEQ ID NO:9:

```
CAGTGATGAT TGGTCGCGGG GCGCTCAATA TTCCCAACCT GAGCCGGGTG GTAAAATATA      60

ACGAACCGCG AATGCCGTGG CCGGAGGTGG TTGCTTTGCT GCAAAAATAT ACCCGTCTGG     120

AAAAGCAGGG CGATACCGGG TTATATCACG TTGCGCGGAT TAAACAGTGG TTGA          174
```

(2) INFORMATION FOR SEQ ID NO:10:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2088 lower (xi) SEQUENCE DESCRIPTION: SEQ ID NO:10:

```
CCGAATCGGA GGCGGTAATA ATCGCAACCT GTGCCATCGA GTTCTCCACT TAACGCTGAA      60

TAAACGTTAA GTATAGAAGG CGCATATCAT CAGCGTTTGT ACCCCCCGCC CAACGCACCA     120

GTGAGTTGAA TGGAGGCATC CAGCCACTGC CCTTGCAATA ACAGGCCATT GGCCCGCTCA     180

CGCAGCGCGG GGATTCTGGC TTCGCTGACG CGGGAACCA                            219
```

(2) INFORMATION FOR SEQ ID NO:11:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2089 upper (xi) SEQUENCE DESCRIPTION: SEQ ID NO:11:

```
GATTTGCTAT CGAAACCATT CTCATTTTTG TGACAGGTTC GTCGTCACTA TATGGCTACG      60

ATAAATAAGG GTGGTAAGCA TTAACAATCC AGGGTAATGG GTGAGGCGAG AGTAAGACGG     120

TAACAGACAT ATCTTCTTGT GTCTTTCTTT TAATACCAAA ACATAACCGT TCTTACATT      180

GATAAAAAAT GGAAAAAGTT GAACACTAGT TGGCGAAAAA TCTTGTATA                 229
```

(2) INFORMATION FOR SEQ ID NO:12:

(i) SEQUENCE CHARACTERISTICS:
        (A) LENGTH: 205 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2089 lower (xi) SEQUENCE DESCRIPTION: SEQ ID NO:12:

```
TAACCCATTA ATTATTGAGC ATAATGTAGG CAGTACAAAA TAAGTTAGGC GGGATATCAG    60

GCGTCAAGAA TGGAACGAGA ACTCTCCATT CTTGACACCT GATATTGCGG ACATAATAAG   120

AAAGCATAAC GCCTGAAATG CTCACTTTGC ATCAGCATGG TGATACAGCT GATGTTTATT   180

CTAAAACCTT ACTCAAGTTC TAAGA                                         205
```

(2) INFORMATION FOR SEQ ID NO:13:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2090 upper (xi) SEQUENCE DESCRIPTION: SEQ ID NO:13:

```
GCTTTCCGAA GAGGGCGCGG TGCAGGTGTT CCGTCCAATC TCCAACAACG ATCTGATCGT    60

TGGTGCAGTT GGTGTGCTGC AGTTTGATGT GGTGGTAGCG CGCCTGAAGA GCGAATACAA   120

CGTTGAAGCA GTGTATGAGT CAGTCAACGT TGCCACTGCC CGCTGGGTAG AATGTGCAGA   180

CGCGAA                                                              186
```

(2) INFORMATION FOR SEQ ID NO:14:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (B) STRAIN: dpd2090 lower (xi) SEQUENCE DESCRIPTION: SEQ ID NO:14:

```
CACCAGGGCC GCCTTCACTT TCGCGGTGAT GGCGCTGTCA TCCATGAAAT TACCGACTTT    60

ATTCATAGAG CTATCGACTT TTTGCCCTGC GCTTTCATTG GTAGTCTGCG CGTTGTTTTC   120

CGCGTAGGCA GAGCCGGTCG CGACGGCAGA GGTCAACATT ACAGCCAGCA GAGTTTTCGA   180

AATCTTCAGT CTTGTCATAG TCATCGATTT ATTCCTGTAT GTTTGCTCGT AATTTGAGCC   240

TGGCAACACG AGGTTGCATT GCTGAATAGG GAGAGACTTC ACCCTCTACA GAAGTCAATG   300

GTCGCCATCA CAAAAGCGAT GAGTGATGAA TAACGACCAT TACAGCCTCT GAATCAGTTA   360

TTAATATCGG TAGAATGACA ATCGACGGCT TTAGATACTG ATATCTACGC ATTGAACGGT   420
```

```
ATTTAACGCC GTCAGAAATG TCATCACTTT GTTAAATATA GATCACAATT TTGAAACCGC    480

TCGGGATATC ACGAAACATA ACAAAAT                                         507

(2) INFORMATION FOR SEQ ID NO:15:

(i) SEQUENCE CHARACTERISTICS:
        (A) LENGTH:  428 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  dpd2092 upper (xi) SEQUENCE DESCRIPTION:  SEQ ID NO:15:

CAAGCCGGTT AACGACCTGT CCCGTGGCGC ACTGGTTGAC GATATCGTCT ACACCATCGC     60

GCTGACTGCG ATTCAGTCTG CACAGCAGCA GTAATCTCGC ATCATCCGCA GCTTTGCGCT    120

GCGGATATCT GAACCGGAAA TAATCACTAT TTCCGGTTTT TTATTCTCTT AATTTGCATT    180

AATCCTTTCT GATTATCTTG CTTAACTGCG CTGCATCAAT GAATTGCGCC ATCCCACTTT    240

GCATACTTAC CACTTTGTTT TGTGCAAGGG AATATTTGCG CTATGTCCGC AATCACTGAA    300

TCCAAACCAA CAAGAAGATG GGCAATGCCC GATACGTTGG TGATTATCTT TTTTGTTGCT    360

ATTTTAACCA GCCTTGCCAC CTGGGTAGTT CCGGTGGGGA TGTTTGACAG TCAGGAAGTG    420

CAGTATCA                                                             428

(2) INFORMATION FOR SEQ ID NO:16:

(i) SEQUENCE CHARACTERISTICS:
        (A) LENGTH:  554 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  dpd2092 lower (xi) SEQUENCE DESCRIPTION:  SEQ ID NO:16:

AGGCCAATCA GAGTGGCGAT AACCCACACC ACGATGCGCA ACCCGGAGCC AGAAAGCACC     60

GGAACGCCGG CAATCCCCTG AGCAACGACC ACACAAAACG GGTTCATCCA CGAACTGGCA    120

AAACCGATTT GCGTGGCAAT ATAGGTCACC AGGACGGTGG TAATACTGTC ATAGCCCAGC    180

CGGACCATTA GCGGTGCGAT GATAATGGCA AAGGCGACGG CCTCTTCTCC CATACCAAAT    240

ACCGCGCCGC CAAGTGAAAA CAGAATAAAC AGCGCAGGAA TAAAGAGAAT TCATTCCCG     300

CGGGTATGGC GAATAAGCGC CAGGATACCG TTATCAATGG TTCCTGTACG CATCACAATG    360

CCAAACGCGC CGCCAATCAC CAGCATAAAC ATGATGATGC CAACGGCTGT CCCGTATTTC    420

GATCCTGAAG TTAATCCTTC AAACGGGAAT TCATCAGCCC GGGCGTTCAT CGCCCGTCGT    480

GAACAGCTGT ACGCGGTGAT ACTCAGGTTC CCTGCTTCGT AATCAAATGC AAATGATTTT    540

GATCTACAAT TTGC                                                       554

(2) INFORMATION FOR SEQ ID NO:17:

(i) SEQUENCE CHARACTERISTICS:
        (A) LENGTH:  87 base pairs
        (B) TYPE:  nucleic acid
        (C) STRANDEDNESS:  single
```

```
            (D) TOPOLOGY:  linear (ii) MOLECULE TYPE:  DNA (genomic)

(vi) ORIGINAL SOURCE:
         (B) STRAIN:  dpd3501 upper (xi) SEQUENCE DESCRIPTION:  SEQ ID NO:17:

GGTCACTTAC TAGGTTATCG GGCCGGTGAT GTCCGACCTC ATGGGCGGGC TGCTCCACTT        60

CCTGAATACC ATTCCTCCAT CAATGAA                                           87

(2) INFORMATION FOR SEQ ID NO:18:

(i) SEQUENCE CHARACTERISTICS:
        (A) LENGTH:  134 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
         (B) STRAIN:  dpd3501 lower (xi) SEQUENCE DESCRIPTION:  SEQ ID NO:18:

ACGACGTCCG GTTTAATGTG TTCCGCCGAG GTTTGCGCCC CGCGTAGCCC AACTTCTTCT        60

TCCACACTGC CAACGCCATA CAGCGTAATT TCGGGATTAT TCACCGTCTG CAATAGTTCA       120

GCCATCATTG CGCA                                                        134

(2) INFORMATION FOR SEQ ID NO:19:

(i) SEQUENCE CHARACTERISTICS:
        (A) LENGTH:  203 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
         (B) STRAIN:  dpd3505 upper (xi) SEQUENCE DESCRIPTION:  SEQ ID NO:19:

TATGGTTTAT CGCTGGTGGG ATTCGGTCTG TTGATTTCAT CACTCTGTTC AACACAACAG        60

CAGGCGTTTA TCGGCGTGTT TGTCTTTATG ATGCCCGCCA TTCTCCTTTC CGGTTACGTT       120

TCTCCGGTGG AAAACATGCC GGTATGGCTG CAAAACCTGA CGTGGATTAA CCCTATTCGC       180

CACTTTACGG ACATTACCAA GCA                                              203

(2) INFORMATION FOR SEQ ID NO:20:

(i) SEQUENCE CHARACTERISTICS:
        (A) LENGTH:  410 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
         (B) STRAIN:  dpd3505 lower (xi) SEQUENCE DESCRIPTION:  SEQ ID NO:20:

CTGTCCAGTC GTAGTAGAGG AAATTGCACC GGAAACGTGC GCGCCGGGCG TCCGTGGGCG        60

CGGGTAAAAA TCTCATCCAG TCCGGCCTGC ACTTTTAACG GATGATTAGC TTTTTGCCGC       120
```

```
CAGTCATTGA AATCACCCGC CACCAATACC GGTTCGCCGT CCGGTAGCTC ATTCACCCAT      180

TCGGCGAGCA TCGCAAGCTG CGCCTGACGG TGCGCCTCAC GCAGGCCCAG ATGTACGCAC      240

ATCACATGAA TCGCTTTTCC GGTCATCGGC GGCACAATGC GGCAGTAGAG CACGCCGCGC      300

TTTTCCGCAC CATCGACCGA AACATCGCGA TTCTCATAAT GTTCAATGGG ATAACGCGAC      360

AGTACGGCGT TGCCGTGATG CCCTTCCGGG TATACGGCAT TGCGACCGTA                410

(2) INFORMATION FOR SEQ ID NO:21:

(i) SEQUENCE CHARACTERISTICS:
          (A) LENGTH:  164 base pairs
          (B) TYPE:  nucleic acid
          (C) STRANDEDNESS:  single
          (D) TOPOLOGY:  linear (ii) MOLECULE TYPE:  DNA (genomic)

(vi) ORIGINAL SOURCE:
          (B) STRAIN:  dpd3507 upper (xi) SEQUENCE DESCRIPTION:  SEQ ID NO:21:

GCCGTTACAC ACGCTGCCAC TGGCAACCAA AGTCCCGGAA CCCTTACCGC CGCTGGAAGG       60

ATACACCTTT GAGGGCTACG CAATGCCGAT GGCAGCGTGG GCACCAAAAA CCTGCTCGGT      120

ATCACCACCA GCGTCCACTG TGTGGCAGGC GTGGTGGACT ATGT                      164

(2) INFORMATION FOR SEQ ID NO:22:

(i) SEQUENCE CHARACTERISTICS:
          (A) LENGTH:  285 base pairs
          (B) TYPE:  nucleic acid
          (C) STRANDEDNESS:  single
          (D) TOPOLOGY:  linear (ii) MOLECULE TYPE:  DNA (genomic)

(vi) ORIGINAL SOURCE:
          (B) STRAIN:  dpd3507 lower (xi) SEQUENCE DESCRIPTION:  SEQ ID NO:22:

CTCCTGTTCA TCTCCCAGTC GGCACATAAA TACTTGCCCA CCAGGCAGAA TTTCGTAATG       60

AATGCTGTCC TGGCCTGGCT TCAGTTTTAA GGCCTCACGC ACTGGCGCGG GGATAGTTGT      120

TTGTCCGCGT ATCGTGACCT TGATTCAGT GGTCAGTACA GCGTGAGAGC GAGCATTAGC      180

GGGCATGATT CACTGTCCTT TTACAGCCTG TTTTCTGCTC AAATTATAAG CTTGAACTAA      240

GGTAATGCAA ATGCATTATT AATGGACGTG GGGGCTTTAA ACAAT                     285

(2) INFORMATION FOR SEQ ID NO:23:

(i) SEQUENCE CHARACTERISTICS:
          (A) LENGTH:  223 base pairs
          (B) TYPE:  nucleic acid
          (C) STRANDEDNESS:  single
          (D) TOPOLOGY:  linear (ii) MOLECULE TYPE:  DNA (genomic)

(vi) ORIGINAL SOURCE:
          (B) STRAIN:  dpd3509 upper (xi) SEQUENCE DESCRIPTION:  SEQ ID NO:23:

GATGGAGTGG CGTAACTATC CGGTAACGCT GGTGGCAGAA AATAACGTTA CCGAAGGCTT       60

TATCGCTGGT CGTCTCACTC GCGAACTGCT GGCAGGTGTA CCTGACTTAG CTTCACGTAC      120

CGTGATGACC TGCGGCCCGG CTCCGTATAT GGATTGGGTA GAGCAGGAAG TGAAAGCGCT      180
```

```
CGGCGTGACG CGTTTCTTTA AAGAGAAATT CTTCACCCCA GTA                     223

(2) INFORMATION FOR SEQ ID NO:24:

(i) SEQUENCE CHARACTERISTICS:
        (A) LENGTH:  260 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
         (B) STRAIN:  dpd3509 lower (xi) SEQUENCE DESCRIPTION:  SEQ ID NO:24:

TGCTCCGGGC TGGAAACCAG CTCGCAATAG TGACTACATT CGCGGAATAG CTCTTGTGGG    60

TGGGTTTCCT GGAAATAGCC GCTGCCAATT TCGCTGGAGG GAATATGAGC GGCAATCGCC   120

AGTACCGGAA CGTGATTGCG GTGGCAATCG AACAGGCCGT TGATTAAGTG CAGGTTGCCG   180

GGGCCGCACG ATCCGGCGCA GACCGCCAGT TCTCCGCTAA GTTGTGCTTC AGCGCCAGCG   240

GCAAAGGCCG CCACTTCTTC                                              260

(2) INFORMATION FOR SEQ ID NO:25:

(i) SEQUENCE CHARACTERISTICS:
        (A) LENGTH:  172 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
         (B) STRAIN:  dpd3512 upper (xi) SEQUENCE DESCRIPTION:  SEQ ID NO:25:

AATGGAGTTT GACTAATACA GGAATACTAT GAGTCTGAAT TTCCTTGATT TTGAACAGCC    60

GATTGCAGAG CTGGAAGCGA AAATCGATTC TCTGACTGCG GTTAGCCGTC AGGATGAGAA   120

ACTGGATATT AACATCGATG AAGAAGTGCA TCGTCTGCGT GAAAAAAGCG TA           172

(2) INFORMATION FOR SEQ ID NO:26:

(i) SEQUENCE CHARACTERISTICS:
        (A) LENGTH:  527 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
         (B) STRAIN:  dpd3512 lower (xi) SEQUENCE DESCRIPTION:  SEQ ID NO:26:

ACTTTTCCCG CAACACGCTC GCCGCTCATA CCACTTTTAC CCTGGTAGAT CGGATGAAAA    60

TGGGTGTACG GCACCCAGGC AGAATCGAAG TGAATCGACG GGACATCCAG CGTCTGTTTG   120

ATCCAGTCGG TGTTGTAGAG CAAGCCATCA TAGGTGGAGT TGGTGATCAC CGCATGAACC   180

GGCCATTGTG CTTGCGTGGT AGCAGCGACT TTCTCTTCGA TGCTGTCGCG AGTAAATTCA   240

CGGCGCGGGA TCCACCAAG AATCCCCAAC GCATTACGCG TCGGTTTCAG CCAGACTGGC   300

ACTACATCGT TCATCATCAA CAGATGCGCC AGCGATTTAT GACAATTGCG GTCGATCAAC   360
```

-continued

```
AGCGTACTGC CGGATGGCGC GGCGTACATA CCCACAATTT TGTTCGACGT CGATGTTCCG      420

TTGGTAACGA TATAACTCTG TTCCGCCCAA AATCCCGCGA TTACTCTTCC GCTTCCAGTG      480

TTGCCCGTGT TGTCAACAAC AACAACTCGG TGACCGAAAT AAAACTC                    527

(2) INFORMATION FOR SEQ ID NO:27:

(i) SEQUENCE CHARACTERISTICS:
        (A) LENGTH:  20 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  upper primer (xi) SEQUENCE DESCRIPTION:  SEQ ID NO:27:

GGATCGGAAT TCCCGGGGAT                                                   20

(2) INFORMATION FOR SEQ ID NO:28:

(i) SEQUENCE CHARACTERISTICS:
        (A) LENGTH:  20 base pairs
        (B) TYPE:  nucleic acid
        (C) STRANDEDNESS:  single
        (D) TOPOLOGY:  linear (ii) MOLECULE TYPE:  DNA (genomic)

(vi) ORIGINAL SOURCE:
        (B) STRAIN:  lower primer (xi) SEQUENCE DESCRIPTION:  SEQ ID NO:28:

CTGGCCGTTA ATAATGAATG                                                   20
```